US010640513B2

(12) United States Patent
Yoon et al.

(10) Patent No.: US 10,640,513 B2
(45) Date of Patent: May 5, 2020

(54) COMPOUND AND COMPOSITION FOR DETECTING PHOSGENE AND DIETHYL CHLOROPHOSPHATE

(71) Applicant: EWHA UNIVERSITY—INDUSTRY COLLABORATION FOUNDATION, Seoul (KR)

(72) Inventors: Juyoung Yoon, Seoul (KR); Xin Zhou, Seoul (KR); Ying Hu, Seoul (KR); Liyan Chen, Seoul (KR)

(73) Assignee: EWHA UNIVERSITY - INDUSTRY COLLABORATION FOUNDATION, Seoul (KR)

( * ) Notice: Subject to any disclaimer, the term of this patent is extended or adjusted under 35 U.S.C. 154(b) by 268 days.

(21) Appl. No.: 15/440,748

(22) Filed: Feb. 23, 2017

(65) Prior Publication Data

US 2017/0240557 A1    Aug. 24, 2017

Related U.S. Application Data

(63) Continuation of application No. PCT/KR2017/001389, filed on Feb. 8, 2017.

(30) Foreign Application Priority Data

Feb. 24, 2016  (KR) .......................... 10-2016-0022097
Feb. 3, 2017   (KR) .......................... 10-2017-0015648

(51) Int. Cl.
*C07D 491/00*  (2006.01)
*C07D 491/107* (2006.01)
(Continued)

(52) U.S. Cl.
CPC ....... *C07D 491/107* (2013.01); *C07D 209/14* (2013.01); *C07D 221/14* (2013.01);
(Continued)

(58) Field of Classification Search
CPC .................................................. C07D 491/107
(Continued)

(56) References Cited

U.S. PATENT DOCUMENTS

2002/0189032 A1   12/2002   Pasquier et al.
2012/0183984 A1    7/2012   He et al.

OTHER PUBLICATIONS

Kumar et al. "A reaction based turn-on type fluorogenic and chromogenic probe for the detection of trace amount of nitrite in water" *Talanta* 99:610-615 (2012).
(Continued)

*Primary Examiner* — Christopher Adam Hixson
*Assistant Examiner* — Emily R. Berkeley
(74) *Attorney, Agent, or Firm* — Klarquist Sparkman, LLP

(57) ABSTRACT

The present invention relates to a compound for detecting phosgene and DCP (diethyl chlorophosphate) and a composition for detecting phosgene and DCP (diethyl chlorophosphate) comprising the said compound. More precisely, the compound for detecting phosgene and DCP of the present invention can selectively detect phosgene and DCP either in the liquid phase of gas phase by detecting the changes of fluorescence and color development very quickly within a few seconds with nM sensitivity. Therefore, the compound can also be effectively used as an ingredient for the composition and kit for the detection of one or more materials selected from the group consisting of phosgene and DCP.

14 Claims, 16 Drawing Sheets

(51) Int. Cl.
    C07D 311/88    (2006.01)
    C07D 221/14    (2006.01)
    C07D 209/14    (2006.01)
    C07D 271/12    (2006.01)
    G01N 31/22     (2006.01)
    G01N 21/77     (2006.01)

(52) U.S. Cl.
    CPC .......... *C07D 271/12* (2013.01); *C07D 311/88* (2013.01); *G01N 31/223* (2013.01); *G01N 2021/7783* (2013.01); *G01N 2021/7786* (2013.01)

(58) Field of Classification Search
    USPC .......................................................... 436/92
    See application file for complete search history.

(56) References Cited

OTHER PUBLICATIONS

Lin et al. "A new selective colorimetric and fluorescent chemodosimeter for $HSO_4$ based on hydrolysis of Schiff base" *Molecular and Biomolecular Spectroscopy* 115:552-558 (2013).

Sun et al. "A Mitochondria-Targetable Fluorescent Probe for Dual-Channel NO Imaging Assited by Intracellular Cysteine and Glutathione" *JACS* 136:12520-12523 (2014).

Wang et al. "Screening and investigation of a cyanine fluorescent probe for simultaneous sensing of glutathione and cysteine under single excitation" *Chem. Commun.* 50:15439-15442 (2014).

Gupta et al. "An Approach for the Selective Detection of Nitric Oxide in Biological Systems: An in vitro an in vivo Perspective" *Chem. Asian J.* 11:1020-1027 (2016).

Zhou et al. "A Fluorescent Sensor for Dual-Channel Discrimination between Phosgene and Nerve-Gas Mimic" *Angew. Chem. Int. Ed.* 55:4729-4733 (2016).

Chen et al. "A Fluorescent Sensor for Dual Channel Discrimination between Phosgene and a Nerve gas Mimic" *The International Symposium on Macrocyclic and Supramolecular Chemistry* 3 pages (2016) abstract.

Yoon "Fluorescent Probes for Hypochlorous acid and Phosgene" *5th International Conference on Molecular Sensors and Molecular Logic Gates* 3 pages (2016) abstract.

Hu et al. "Effective Strategy for Colorimetric and Fluorescence Sensing of Phosgene Based on Small Organic Dyes and Nanofiber Platforms" *American Chemical Society* 8:22246-22252 (2016).

Ying "Small Organic Dyes and Nanofiber Platforms Based Effective Strategy for Colorimetric and Fluorescence Sensing of Phosgene" *The 118th General Meeting of the Korean Chemical Society* 2 pages (2016) abstract.

Sarkar and Shunmugam "Polynorbornene derived 8-hydroxyquinoline paper strips for ultrasensitive chemical nerve agent surrogate sensing" *ChemComm* 50:8511-8513 (2014).

Figure 3(a)
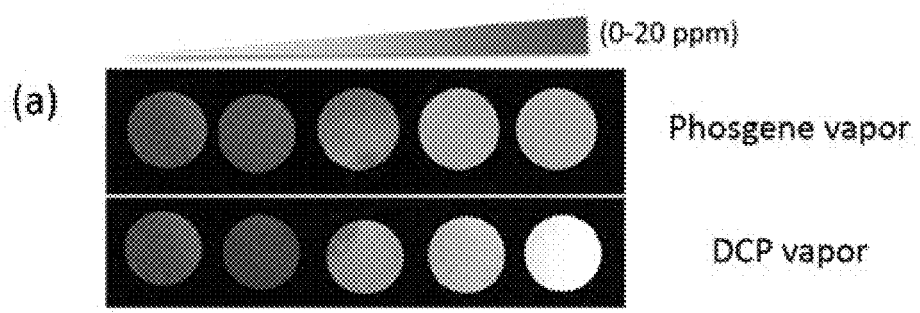
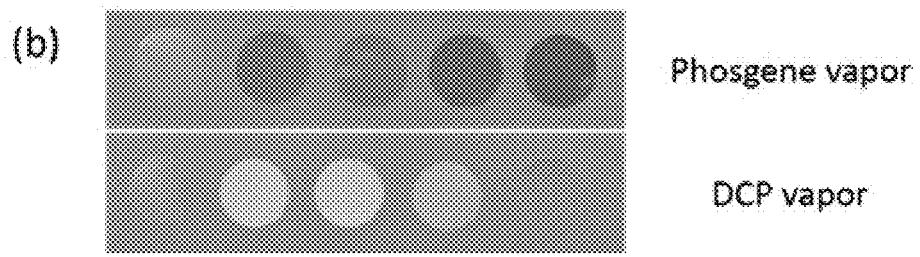
Figure 3b no phosgene exposure
no fluorescence, black exposed on 0.8 mg/L of phosgene
fluorescence, green exposed on 8 mg/L of phosgene
fluorescence, cyan
(Stronger fluorescence than Figure 7)

no phosgene exposure
no fluorescence, black exposed on 0.8 mg/L of phosgene
fluorescence, dark blue exposed on 8 mg/L of phosgene
fluorescence, blue
(Stronger fluorescence than Figure 10)

COMPOUND AND COMPOSITION FOR DETECTING PHOSGENE AND DIETHYL CHLOROPHOSPHATE

CROSS REFERENCE TO RELATED APPLICATION

This patent application is a continuation of PCT Application No. PCT/KR2017/001389, filed Feb. 8, 2017, which claims the benefit of priority from Korean Patent Application No. 10-2017-0015648, filed Feb. 3, 2017, and Korean Patent Application No. 10-2016-0022097, filed Feb. 24, 2016. The contents of all three of these patent applications is incorporated herein by reference.

TECHNICAL FIELD

The present invention relates to a compound and a composition for detecting phosgene and DCP (diethyl chlorophosphate).

BACKGROUND

Phosgene is a highly toxic gas which is colorless at room temperature. Phosgene sits in top 10% of the most toxic materials. It has also been known as a notorious chemical warfare agent (CWA) since it killed more than 100,000 people as a chemical weapon during World War I.

Once exposed on phosgene, the respiratory system is severely damaged, leading to the disease such as noncardiogenic pulmonary edema and emphysema and even death. Unlike other chemical warfare agents such as Sarin, Soman, Taburn, and DCP (diethyl chlorophosphate), phosgene has a latent period with no apparent symptoms, during which pulmonary edema is developed due to its unique toxicity that leads to death.

There is no method to detect patients exposed on phosgene at the latent stage or to determine the possibility of the development of pulmonary edema thereby. The production of Sarin, Soman, and Taburn is limited by law but phosgene is widely used in industry and used as a starting material for the production of other compounds, insecticides, pharmaceuticals and isocyanate-based polymers. Therefore, there is a relatively high chance of a disaster occurring due to the exposure by an accident or other routes.

So, human lives can be damaged or lost by intentionally induced exposure on phosgene through war or terror or massive civil damage can be induced by the exposure through an industrial accident, making phosgene a highly dangerous material.

Therefore, it is very important to detect phosgene fast and accurately for protecting human lives. It is also necessary to develop a method to detect phosgene selectively from other gases or CWAs.

Sensors are under development to detect CWA by detecting the changes of fluorescence or color development (Santu Sarkar and Raja Shunmugam. Chem. Commun., 2014, 50, 8511-8513). It is still requested to develop a fluorescent chemical sensor or color sensor to detect CWA faster and more sensitively within a few seconds. Moreover, a sensor to detect a target material from other CWAs or gases has not been developed yet.

Thus, the present inventors have developED a method to detect phosgene selectively fast and accurately within a few seconds by detecting the changes of fluorescence or color development. In the course of the study, the present inventors confirmed that the compound of the present invention can detect phosgene and DCP (diethyl chlorophosphate) fast and accurately within a few seconds at even nM unit by screening the changes of fluorescence and color development and can detect phosgene and DCP selectively from other CWAs or gases, leading to the completion of the present invention.

Technical Problem

It is an object of the present invention to provide a compound for detecting phosgene and DCP (diethyl chlorophosphate).

It is another object of the present invention to provide a method for the preparation of the compound above.

It is also an object of the present invention to provide a composition for detecting phosgene comprising the said compound above.

It is further an object of the present invention to provide a composition for the detection of DCP (diethyl chlorophosphate) comprising the said compound above.

It is also an object of the present invention to provide a kit for the detection of one or more compounds selected from the group consisting of phosgene and DCP (diethyl chlorophosphate) which comprises the said compound above.

It is also an object of the present invention to provide a method for the detection of one or more compounds selected from the group consisting of phosgene and DCP (diethyl chlorophosphate) by using the detection kit above.

Technical Solution

To achieve the above objects, the present disclosure provides a compound represented by formula 1 below.

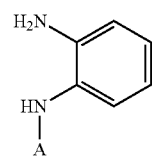

[Formula 1]

wherein

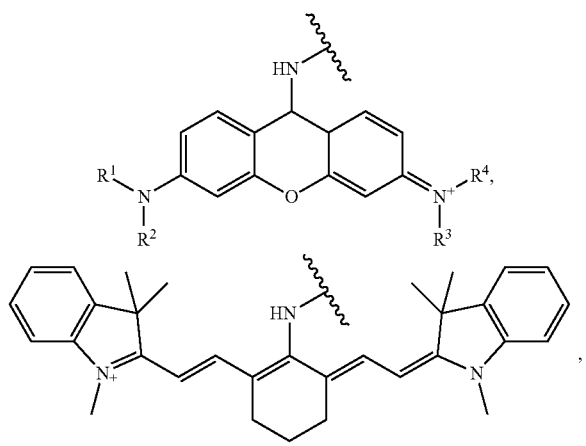

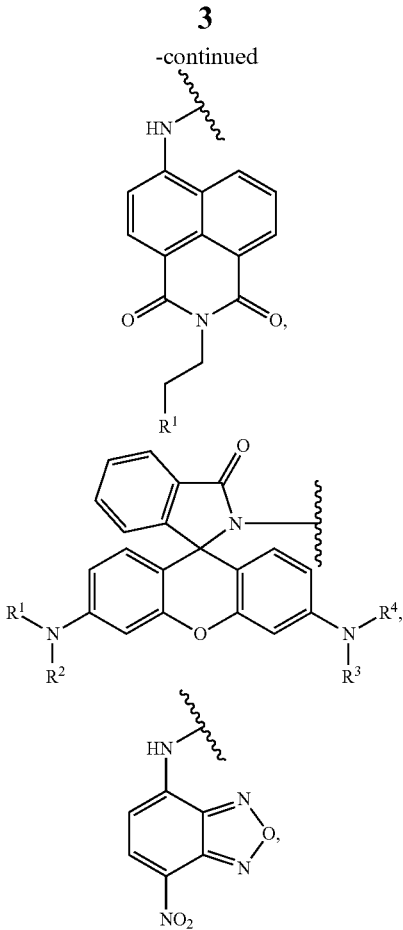

A is

R1 is —H, C1-10 straight or branched alkyl, C1-10 straight or branched alkoxy, or 4-7 membered heterocycloalkyl containing 1-3 hetero atoms selected from the group consisting of N, O, and S; and R2, R3 and R4 is independently —H, C1-10 straight or branched alkyl, or C1-10 straight or branched alkoxy.

The present disclosure also provides a method for preparing the compound represented by formula 1 containing the step of reacting the compound represented by A-LG with the compound represented by formula 2 to give the compound represented by formula 1 (step 1) as shown in the below reaction formula 1.

[Reaction Formula 1]

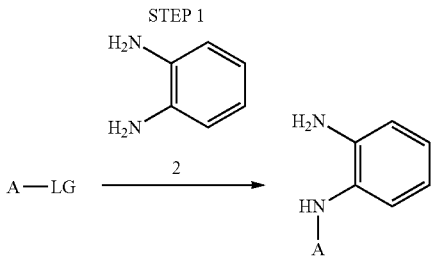

In the reaction formula 1, A is as defined in formula 1; and LG is =O, =S or halogene.

Further, the present disclosure provides a composition for detecting phosgene comprising the compound represented by formula 1.

The present disclosure also provides a composition for the detection of DCP (diethyl chlorophosphate) comprising the compound represented by formula 1.

The present disclosure also provides a kit for the detection of one or more compounds selected from the group consisting of phosgene and DCP (diethyl chlorophosphate) comprising the compound represented by formula 1.

The present disclosure also provides a method for the detection of one or more compounds selected from the group consisting of phosgene and DCP (diethyl chlorophosphate) comprising the following steps:

contacting the detection kit of the invention with the sample to be analyzed (step 1); and evaluating the changes of fluorescence or absorption properties of the compound represented by formula 1 included in the detection kit after the contact of step 1 (step 2).

Advantageous Effects

The compound for detecting phosgene and DCP (diethyl chlorophosphate) of the present disclosure can selectively detect phosgene and DCP (diethyl chlorophosphate) either in the liquid phase or gas phase by detecting the changes of fluorescence and color development very quickly within a few seconds with nM sensitivity. Therefore, the compound can be effectively used as a composition for the detection of one or more compounds selected from the group consisting of phosgene and DCP (diethyl chlorophosphate).

BRIEF DESCRIPTION OF DRAWINGS

The application of the preferred embodiments of the present invention is best understood with reference to the accompanying drawings, wherein:

FIG. 1($b$) is a graph illustrating the absorption spectrum of the compound of example 1 of the invention according to the concentration of phosgene.

FIG. 2($b$) is a graph illustrating the absorption spectrum of the compound of example 1 of the invention according to the concentration of DCP (diethyl chlorophosphate).

FIG. 3($a$) is an image illustrating the changes of fluorescence resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of fluorescence in there.

FIG. 3($b$) is an image illustrating the changes of color development resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of color development in there.

BEST MODE

Figure 1A:
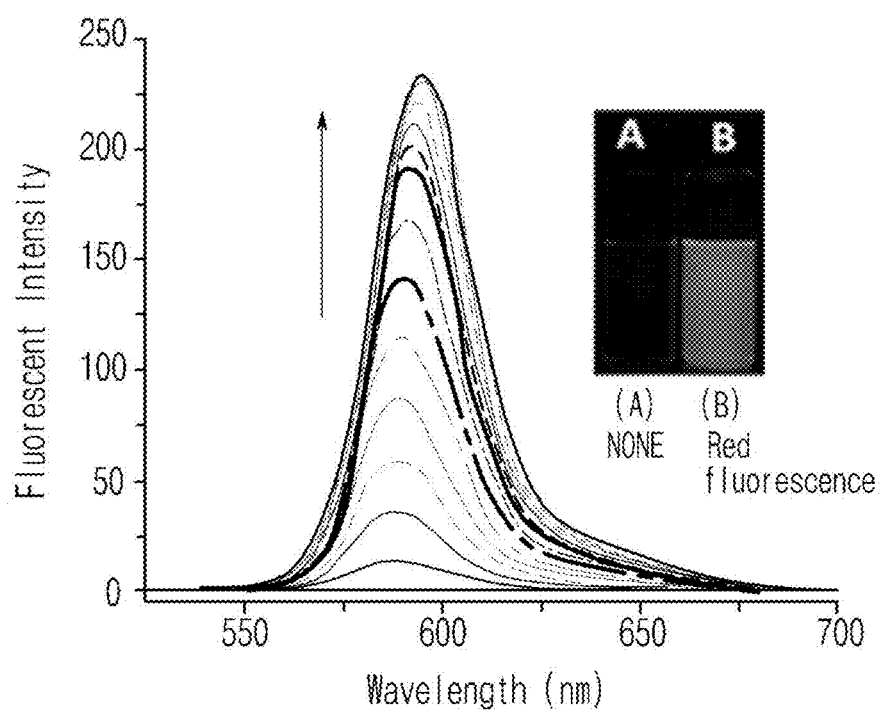
FIG. 1($a$) is a graph illustrating the fluorescence spectrum of the compound of example 1 of the invention according to the concentration of phosgene.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparative Example 1> Preparation of o-phenylenediamine-pyronin (N-(9-(2-aminophenylamino)-6-(dimethylamino)-3H-xanthen-3-ylidene)-N-methylmethanaminium)

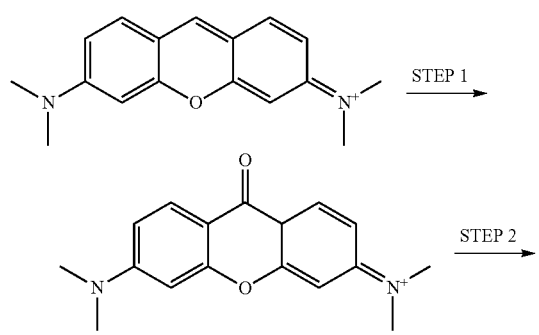

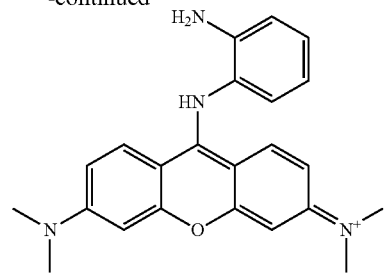

Step 1: Preparation of N-(6-(dimethylamino)-9-oxo-9,9a-dihydroxandene-3-ylidene)-N-methylmethanaminium N-(6-(dimethylamino)-3H-xandene-3-ylidene)-N-methylmethanaminium was reacted with KCN for 18 hours, reacted with FeCl3/HCl for 12 hours, and then reacted with NaHCO3, resulting in the preparation of N-(6-(dimethylamino)-9-oxo-9,9a-dihydroxandene-3-ylidene)-N-methylmethanaminium.

Step 2: Preparation of N-(9-(2-aminophenylamino)-6-(dimethylamino)-3H-xanthen-3-ylidene)-N-methylmethanaminium The compound prepared in step 1 above was reacted with Tf2O and then reacted with benzene-1,2-diamine to give N-(9-(2-aminophenylamino)-6-(dimethylamino)-3H-xanthen-3-ylidene)-N-methylmethanaminium (yield: 40%).

<Example 1> Preparation of Compounds for Detecting Phosgene and DCP 1

Step 1: Preparation of N-(6-(dimethylamino)-9-thioxo-9,9a-dihydroxandene-3-ylidene)-N-methylmethanaminium

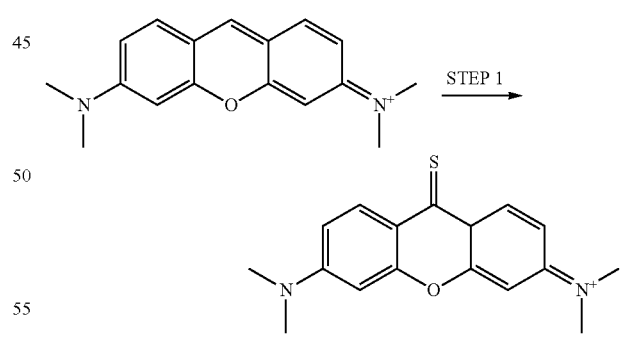

THF (40 ml) containing t-BuOK (0.56 g, 3 eq) was added to the solution containing Pyronine Y (N-(6-(dimethylamino)-3H-xandene-3-ylidene)-N-methylmethanaminium) (0.5 g, 1.65 m mol) and sulfur (0.79 g, 15 eq). The reaction mixture was refluxed for 10 hours. Termination of the reaction was confirmed by TLC. Then, the reaction mixture was cooled down at room temperature and filtered. Silica gel column chromatography was performed with the residue (eluent, PE:DCM, 1:1) to give the target compound as a yellow solid (yield: 50%).

1H NMR (300 MHz, CDCl3), δ: 8.70 (d, J=9.2 Hz, 2H), 6.75 (dd, J=9.2, 2.3 Hz, 2H), 6.43 (d, J=2.3 Hz, 2H), 3.13 (s, 12H). 13C NMR (75 MHz, CDCl3), δ: 196.26, 154.58, 153.03, 131.80, 120.07, 110.52, 96.06, 40.24. ESI-MS: Calcd. for 299.11; Found 299.20.

Step 2: Preparation of N-(9-(2-aminophenylamino)-6-(dimethylamino)-3H-xanthen-3-ylidene)-N-methylmethanaminium

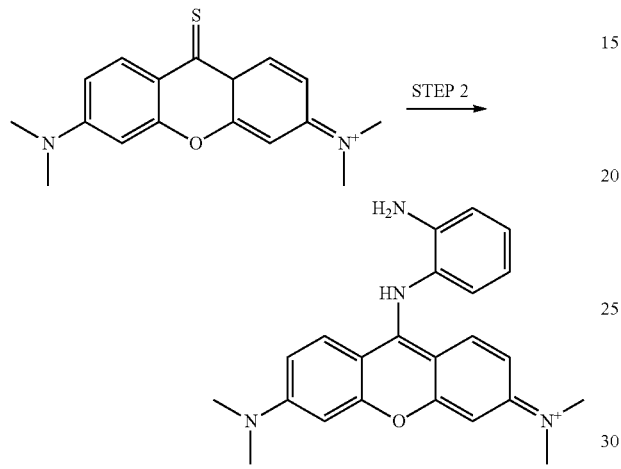

90 μl (2 eq) of Tf2O was added drop by drop to the anhydrous CH2Cl2 solution (10 ml) containing 80 mg (0.268 m mol) of the compound prepared in step 1 above dissolved therein. The reaction mixture was well mixed with stirring at room temperature for 10 minutes. 0.29 g (10 eq) of o-phenylenediamine solution was added to the reaction mixture above, followed by stirring for 10 more hours. Then, CH2Cl2 was eliminated under reduced pressure. The solid residue was purified by silica gel chromatography (eluent, EA:DCM, 1:2) to give the target compound as a yellow solid (yield: 80%).

1H NMR (300 MHz, MeOD), δ: 7.78 (d, J=9.5 Hz, 2H), 7.25 (m, 1H), 7.09 (dd, J=7.8, 1.4 Hz, 1H), 6.96 (dd, J=7.8, 1.4 Hz, 1H), 6.81 (dd, J=3.9, 1.9 Hz, 1H), 6.76 (m, 2H), 6.71 (d, J=2.5 Hz, 2H), 3.18 (s, 12H). 13C NMR (75 MHz, MeOD), δ: 157.01, 155.46, 154.03, 147.21, 143.91, 129.31, 126.98, 126.52, 117.72, 116.26, 110.67, 102.83, 96.68, 38.80. ESI-MS: [M]+Calcd. for 372.20; Found 372.30.

<Example 2> Preparation of Compounds for Detecting Phosgene and DCP 2

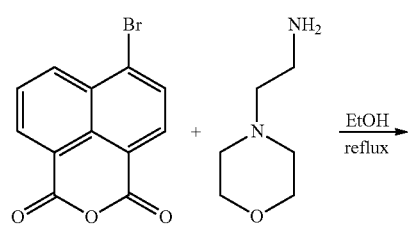

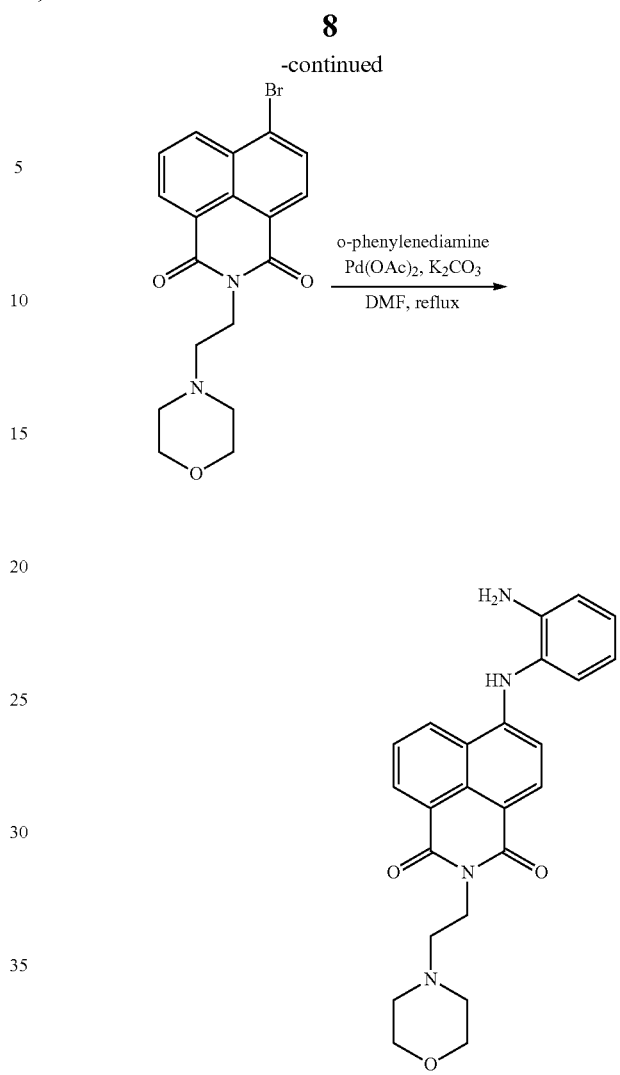

To a solution of 4-bromo-1,8-naphthalene anhydride (1.38 g, 5.0 mmol) in anhydrous EtOH (20.0 ml) at room temperature was added 4-(2-aminoethyl)morpholine (715 mg, 5.5 mmol). After refluxing for 4 h, the reaction mixture was cooled and filtered to give 4-bromine-1,8-naphthalimide. This naphthalimide (389 mg, 1.0 mmol) and o-phenylenediamine (540 mg, 5.0 mmol) were dissolved in anhydrous DMF (20 mL), Subsequently, K2CO3 (550 mg, 4 mmol) and Pd(OAc) (44 mg, 2 mmol) was added under nitrogen. The reaction was then refluxed overnight. The solvent DMF was then removed under vacuum. The crude product was treated with water, extracted with dichloromethane and dried over anhydrous MgSO4. The organic layer was removed and the residue was purified by column chromatography to give 0.18 g of product (yellow solid, 43%).

1H NMR (CDCl3, 300 MHz) δ (ppm)=8.59 (m, 1H), 8.35 (d, 1H), 8.28 (d, 1H), 7.69 (m, 1H), 7.17 (m, 2H), 6.92-6.77 (m, 2H), 6.67 (d, 1H), 6.53 (s, 1H), 4.37-4.23 (m, 2H), 3.79 (s, 2H), 3.71-3.88 (m, 4H), 2.72-2.61, 2H), 2.57 (s, 4H). 13C NMR (75 MHz, CDCl3) δ=164.51, 163.89, 147.49, 142.82, 133.96, 131.31, 128.32, 127.44, 126.22, 125.32, 124.50, 123.21, 120.74, 119.50, 116.75, 112.30, 107.75, 67.02, 56.23, 53.80, 36.98. HRMS (ESI) m/z=417.1718 [M+H]+, calcd for C24H25N4O3=417.1927.

<Example 3> Preparation of Compounds for Detecting Phosgene and DCP 3

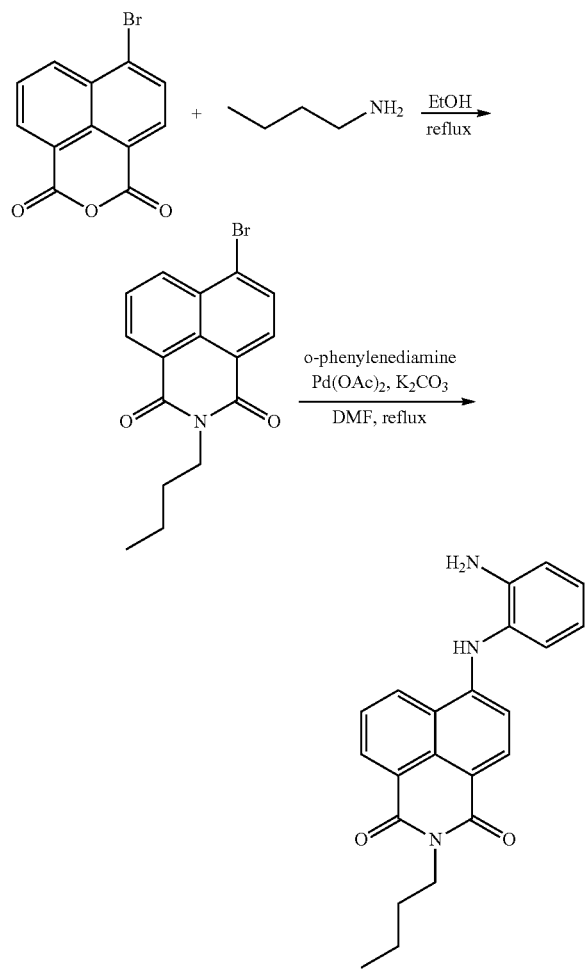

To a solution of 4-bromo-1,8-naphthalene anhydride (1.38 g, 5.0 mmol) in anhydrous EtOH (20.0 ml) was added butylamine (480 mg, 5.5 mmol) at room temperature. After refluxing for 4 h, the reaction mixture was cooled and filtered to give 4-bromine-1, 8-naphthalimide. This naphthalimide (540 mg, 5.0 mmol) and o-phenylenediamine (540 mg, 5.0 mmol) were dissolved in anhydrous DMF (20 mL), Subsequently, K2CO3 (550 mg, 4 mmol) and Pd(OAc) (44 mg, 2 mmol) under nitrogen. The reaction was then refluxed overnight. The solvent DMF was then removed under vacuum. The crude product was treated with water, extracted with dichloromethane and dried over anhydrous MgSO4. The organic layer was removed and the residue was purified by column chromatography to give 0.11 g of product (yellow solid, 61%).

1H NMR (DMSO-d6, 300 MHz) δ (ppm)=9.01 (s, 1H), 8.91-8.88 (m, 1H), 8.50-8.47 (m, 1H), 8.20 (d, J=8.6 Hz, 1H), 7.78-7.73 (m, 1H), 7.09 (t, J=7.2 Hz, 2H), 6.88-6.84 (m, 1H), 6.69-6.63 (m, 1H), 6.41 (d, J=8.5 Hz, 1H), 5.04 (s, 2H), 4.16-3.89 (m, 2H), 1.58 (d, J=7.5 Hz, 2H), 1.47-1.19 (m, 2H), 0.92 (t, J=7.3 Hz, 3H); 13C NMR DMSO-d6, 6=164.47, 163.63, 150.48, 145.65, 134.54, 131.47, 130.23, 130.05, 128.82, 128.44, 125.14, 123.99, 122.55, 121.34, 117.19, 116.35, 109.79, 107.01, 55.61, 30.53, 20.51, 14.46. HRMS (ESI) m/z=360.1706 [M+H]+, calcd for C24H25N4O3=360.1712.

<Example 4> Preparation of Compounds for Detecting Phosgene and DCP 4

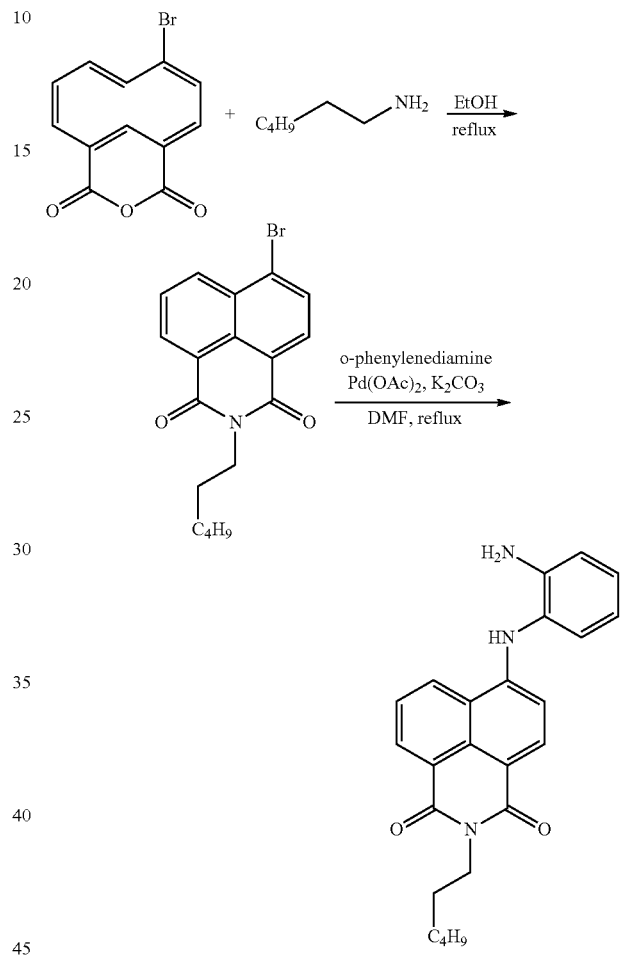

The target compound was prepared by conducting the same synthesis as in Example 3 except that hexylamine was used instead of the butylamine used in Example 3.

<Example 5> Preparation of Compounds for Detecting Phosgene and DCP 5

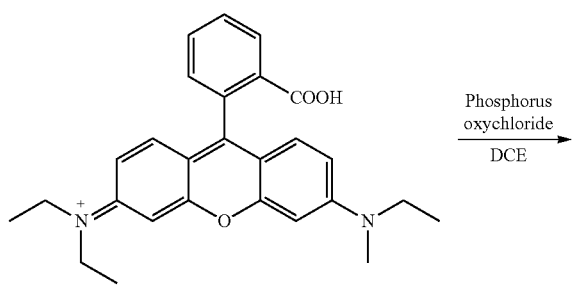

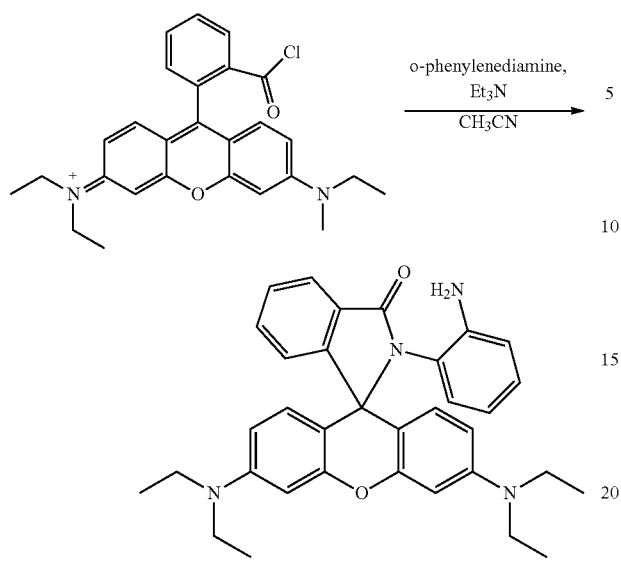

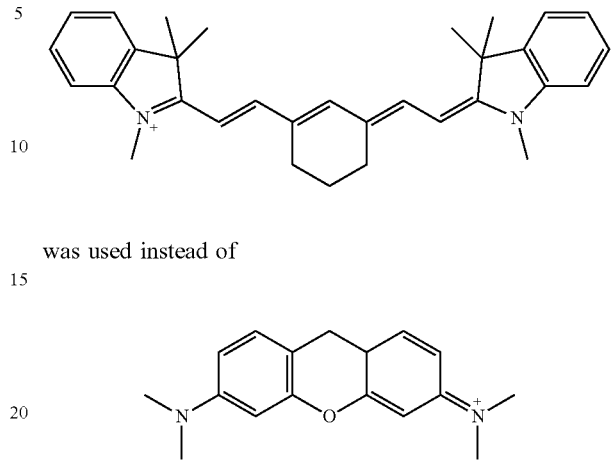

in the step 1 of Example 1 above.

<Example 7> Preparation of Compounds for Detecting Phosgene and DCP 7

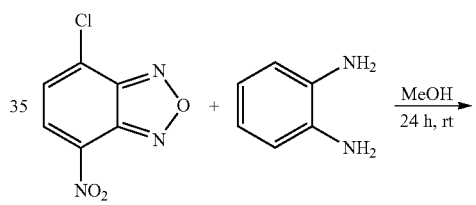

To a solution of rhodamine B base (1.01 g, 2.3 mmol) in dry 1,2-dichloroethane (8.0 mL) at room temperature was added phosphorus oxychloride (6.9 mmol) over a period of 5 min. After being stirred at reflux for 4 h, the mixture was cooled and concentrated under vacuum to give the crude rhodamine B acid chloride. A solution of the acid chloride in dry acetonitrile (10 mL) was added dropwise to a solution of o-diaminobenzene (14 mmol) in dry acetonitrile (6.0 mL) containing triethylamine (8.0 mL). After being stirred for 4 h at room temperature, the mixture was concentrated under vacuum, and the residue was subjected to column chromatography to give target compound as a white solid in 83% yield.

1H NMR (CDCl3, 300 MHz) δ (ppm): 8.03-8.05 (m, 1H); 7.53-7.60 (m, 2H); 7.25-7.27 (m, 1H); 6.94-6.99 (m, 1H); 6.68 (d, J=8.7 Hz, 2H); 6.58 (dd, J=7.8 Hz, J=1.2 Hz, 1H); 6.40-6.46 (m, 1H); 6.31 (d, J=8.7 Hz, 2H); 6.28 (b, 2H); 6.10 (dd, J=8.1 Hz, J=1.5 Hz, 1H); 3.44 (s, 2H); 3.35 (q, J=6.9 Hz, 8H); 1.16 (t, J=7.2 Hz, 12H). 13C NMR (CDCl3, 75 MHz) δ (ppm): 166.63, 161.22, 154.20, 152.66, 149.15, 144.75, 132.81, 129.03, 128.97, 128.85, 128.55, 124.51, 123.66, 122.46, 118.43, 117.23, 108.21, 98.28, 68.27, 44.60, 31.15, 12.76. HRMS (ESI) m/z calcd for C34H36N4O2 [M+H]+ 533.2565. Found 533.2838.

<Example 6> Preparation of Compounds for Detecting Phosgene and DCP 6

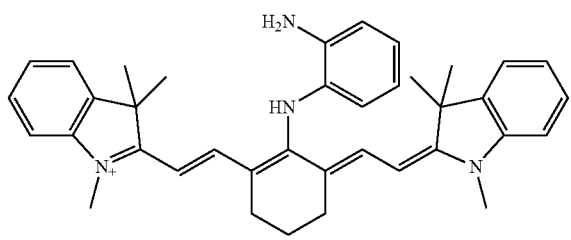

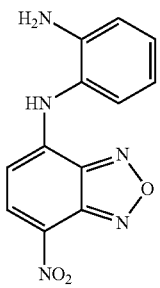

To a solution of o-phenylenediamine (0.32 g, 3.0 mmol) in methanol (10 mL) was added NBD-Cl (0.20 g, 1.0 mmol) in methanol (10 mL) at room temperature with stirring. The resulting mixture was stirred at room temperature for 24 hours. Filtered and washed several times with methanol to give a target compound (reddish brown solid, 71%).

1H NMR (DMSO-d6, 300 MHz): δ 10.69 (brs, 1H), 8.54 (d, J=8.7 Hz, 1H), 7.09-7.15 (m, 2H), 6.84 (d, J=7.2 Hz, 1H), 6.64 (t, J=7.8 Hz, 1H), 5.93 (d, J=8.7 Hz, 1H), 5.27 (brs, 2H). 13C NMR (DMSO-d6, 75 MHz): d 145.49, 145.04, 144.96, 144.92, 138.58, 129.44, 128.14, 121.95, 116.77, 116.49, 113.59, 102.34. HRMS (EI) m/z=270.0640 [M]+, calcd for C12H9N5O3=270.0704.

<Comparative Example 1> Preparation of N-(9-(4-aminophenylamino)-6-(dimethylamino)-9,9a-dihydroxandene-3-ylidene)-N-methylmethanaminium

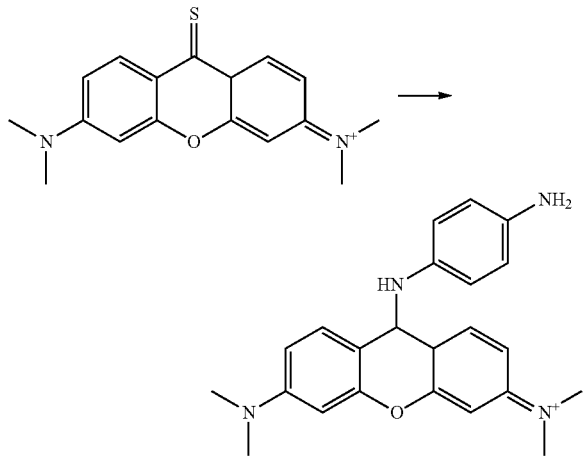

50 mg (0.168 m mol) of the compound prepared in step 1 of example 1 was dissolved in CH2Cl2 (10 ml), to which 57 μl (2 eq) of Tf2O was added drop by drop. The reaction mixture was stirred for 10 minutes, to which 235 μl (15 eq) of phenylamine was added. The mixture was stirred at room temperature for overnight. Upon completion of the reaction, CH2Cl2 was eliminated under reduced pressure. The solid residue was purified by silica gel chromatography (eluent, EA:DCM, 1:3) to give the target compound as an orange solid (yield: 70%).

1H NMR (300 MHz, MeOD), δ: 7.67 (d, J=9.5 Hz, 2H), 7.56 (dd, J=7.7, 6.6 Hz, 2H), 7.46 (m, 1H), 7.40 (d, J=7.7 Hz, 2H), 6.80 (dd, J=9.5, 2.4 Hz, 2H), 6.73 (d, J=2.4 Hz, 2H), 3.19 (s, 12H). 13C NMR (75 MHz, MeOD), δ: 157.34, 155.65, 153.33, 140.66, 129.94, 127.66, 127.16, 125.05, 110.83, 102.73, 96.32, 38.86. ESI-MS: [M]+Calcd for 358.19; Found 358.30.

<Comparative Example 2> Preparation of N-(6-(dimethylamino)-9-(phenylamino)-9,9a-dihydroxandene-3-ylidene)-N-methylmethanaminium

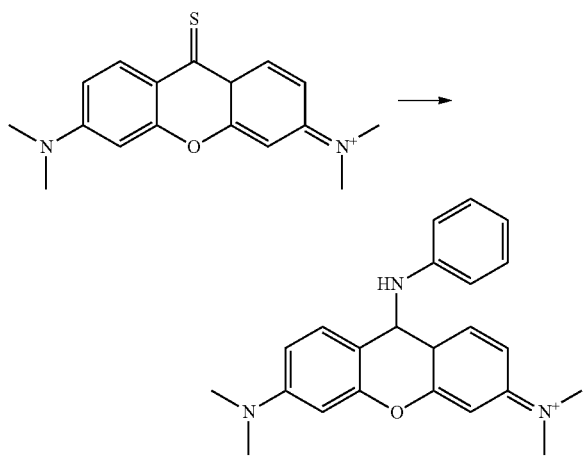

100 mg (0.336 m mol) of the compound prepared in step 1 of example 1 was dissolved in CH2Cl2 (15 ml), to which 114 μl (2 eq) of Tf2O was added drop by drop. The reaction mixture was stirred for 10 minutes, to which 0.54 g (15 eq) of p-phenylenediamine was added. The mixture was stirred at room temperature for overnight. Upon completion of the reaction, the solvent was eliminated under reduced pressure. The solid residue was purified by silica gel chromatography (eluent, DCM:EtOH, 30:1) to give the target compound as a yellow solid (yield: 70%).

1H NMR (300 MHz, MeOD) δ 7.74 (s, 2H), 7.13 (m, 2H), 6.84 (m, 4H), 6.70 (d, J=2.5 Hz, 2H), 3.18 (s, 12H). 13C NMR (75 MHz, MeOD) δ 157.01, 154.99, 150.34, 129.75, 128.51, 127.92, 116.80, 112.16, 103.60, 97.75, 40.26. [M]+ calcd for 373.20, Found 373.30.

<Experimental Example 1> Evaluation of Phosgene Detection Ability of the Compound of Example 1

The following experiment was performed in order to evaluate the phosgene detection ability of the compound prepared in example 1.

Particularly for the safety of the experiment, non-volatile and relatively less toxic triphosgene, the precursor of phosgene, was used instead of the volatile phosgene to evaluate the detection ability of the compound prepared in example 1. The compound of example 1 was loaded in chloroform at the concentration of 10 μM, to which triphosgene was added with different concentrations (0-2 eq), during which the changes of fluorescence and absorbance were observed to evaluate the phosgene detection ability. The results are shown in FIG. 1. In the experiment, excitation wavelength was 580 nm and slit width was 1.5 nm. Each spectrum was measured at 2 min intervals.

Figure 1B:
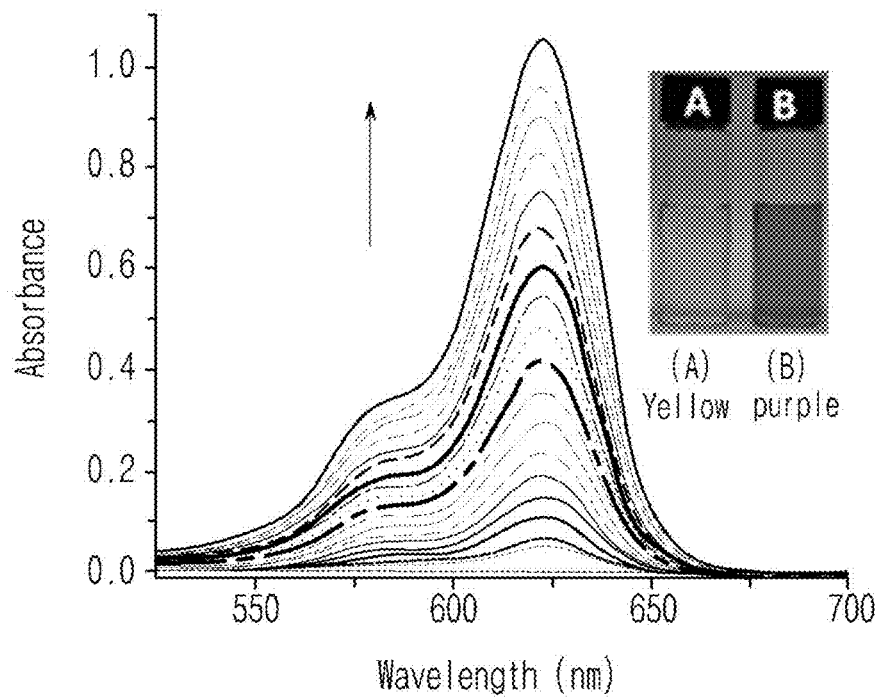

FIG. 1(a) is a graph illustrating the fluorescence spectrum of the compound of example 1 of the invention according to the concentration of phosgene, wherein the fluorescence photograph is on the right side of the graph. FIG. 1(b) is a graph illustrating the absorption spectrum of the compound of example 1 of the invention according to the concentration of phosgene, wherein the color development photograph is on the right side of the graph.

As shown in FIG. 1(a), the fluorescence intensity of the compound of example 1 of the invention was stronger as the concentration of phosgene was increased, and thus red fluorescence was observed with the naked eye. As shown in FIG. 1(b), wavelength band of the absorption spectrum of the compound of example 1 of the invention was changed as the concentration of phosgene was increased. The color thereof started yellow and turned purple, which was also observed with the naked eye.

Therefore, the compound for detecting phosgene of the present invention can be effectively used as a composition for detecting phosgene since the changes of fluorescence and color development can be observed with the naked eye.

<Experimental Example 2> Evaluation of DCP (Diethyl Chlorophosphate) Detection Ability of the Compound of Example 1

The following experiment was performed by the same manner as described in experimental example 1 in order to evaluate the DCP detection ability of the compound prepared in example 1 of the invention except that DCP (diethyl chlorophosphate) was used instead of phosgene. The results are shown in FIG. 2.

Figure 2A:
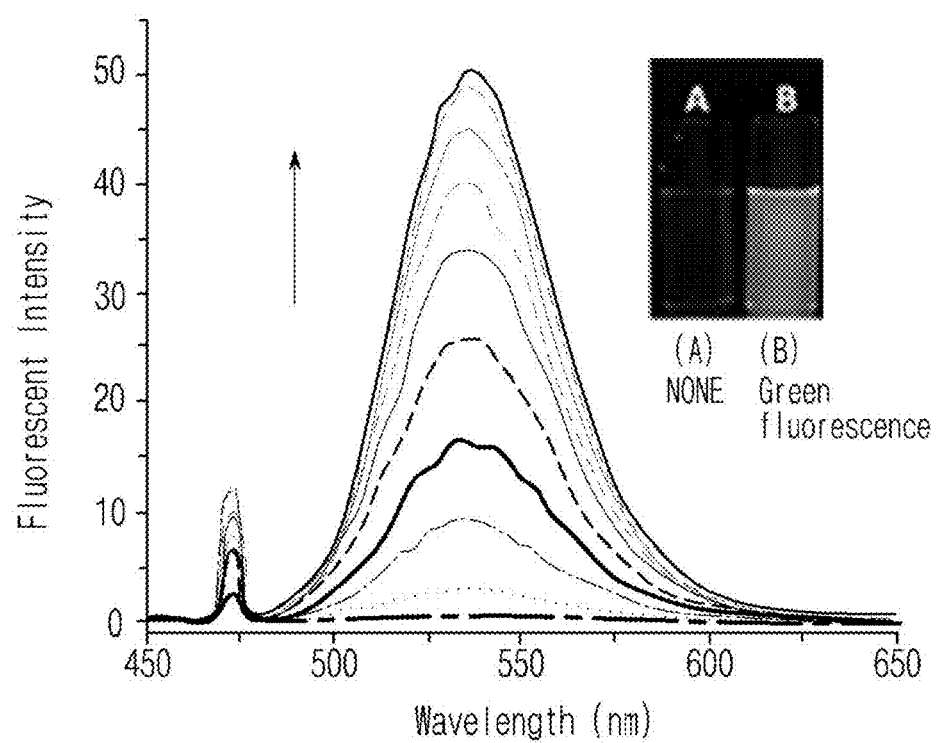
FIG. 2($a$) is a graph illustrating the fluorescence spectrum of the compound of example 1 of the invention according to the concentration of DCP (diethyl chlorophosphate).

FIG. 2(a) is a graph illustrating the fluorescence spectrum of the compound of example 1 of the invention according to the concentration of DCP (diethyl chlorophosphate), wherein the fluorescence photograph is on the right side of the graph.

Figure 2B:
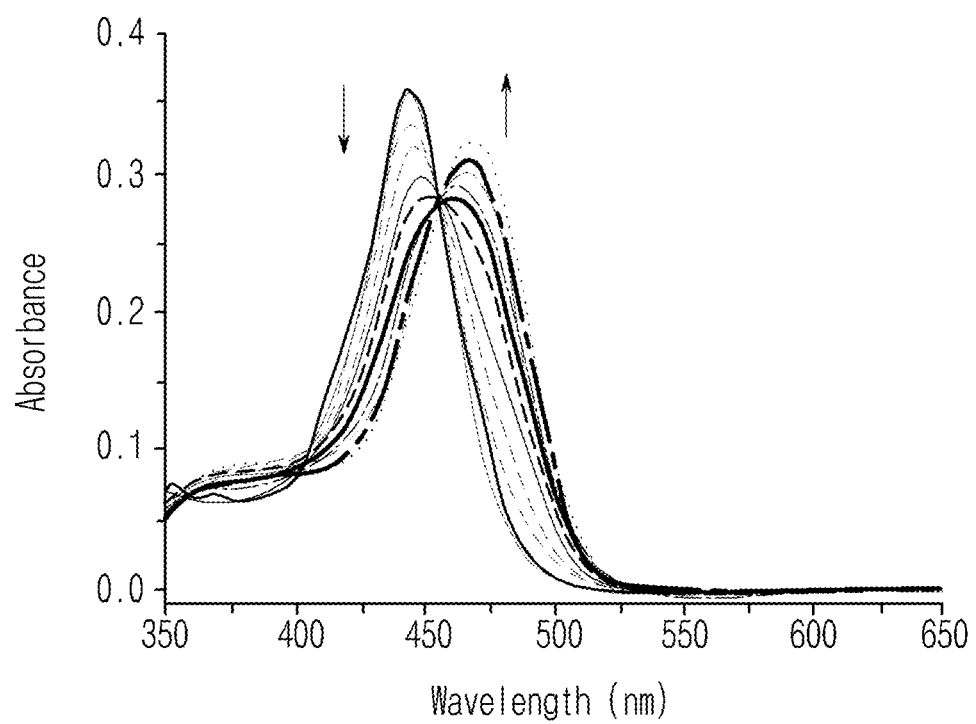

FIG. 2(b) is a graph illustrating the absorption spectrum of the compound of example 1 of the invention according to the concentration of DCP (diethyl chlorophosphate).

As shown in FIG. 2(a), the fluorescence intensity of the compound of example 1 of the invention was stronger as the concentration of DCP (diethyl chlorophosphate) was increased, and thus green fluorescence was observed with the naked eye.

As shown in FIG. 2(b), wavelength band of the absorption spectrum of the compound of example 1 of the invention was changed as the concentration of DCP (diethyl chlorophosphate) was increased.

Therefore, the compound for the detection of DCP (diethyl chlorophosphate) of the present invention can be effectively used as a composition for the detection of DCP (diethyl chlorophosphate) since the changes of fluorescence and color development can be observed with the naked eye.

<Experimental Example 3> Evaluation of Gas-Phase Phosgene and DCP (Diethyl Chlorophosphate) Detection Ability of the Compound of Example 1

The following experiment was performed in order to evaluate the gas-phase phosgene and DCP detection ability of the compound of example 1 of the invention.

Particularly, in order to evaluate whether or not the compound prepared in example 1 could act as a real sensor to detect gas-phase phosgene and DPC efficiently, a kit was constructed wherein the compound of example 1 was fixed on polyethylene oxide film. The kit was exposed on different concentrations of phosgene and DCP (0-20 ppm), followed by observation of the changes of fluorescence and color development in the compound of example 1. The results are shown in FIG. 3.

FIG. 3(a) is an image illustrating the changes of fluorescence resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of fluorescence.

FIG. 3(b) is an image illustrating the changes of color development resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of color development.

As shown in FIG. 3, the compound of the example of the present invention can be useful as a sensor to detect the changes of fluorescence and color development according to the exposure on gas-phase phosgene and DCP (diethyl chlorophosphate).

<Experimental Example 4> Evaluation 1 of Phosgene Detection Ability of the Compound of Example 2

The following experiment was performed to evaluate whether or not the compound of example 2 was useful for the detection of gas-phase phosgene.

Figure 7:
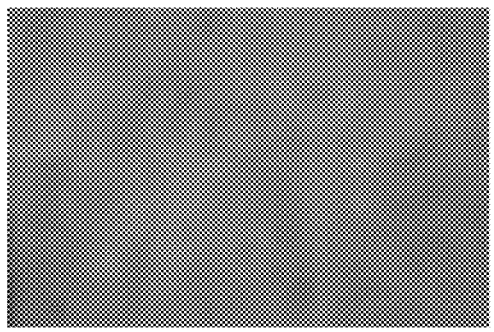
FIG. 7 is a photograph illustrating the image of the filter-paper retaining the compound of example 2 and exposed on 0.8 mg/L of phosgene, photographed at 365 nm.
Figure 8:
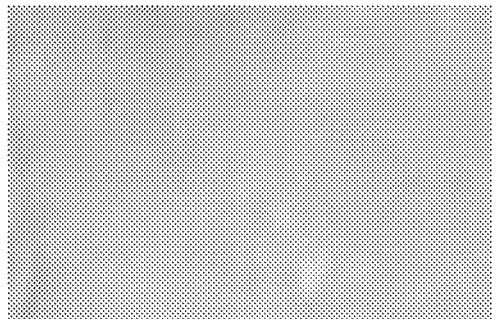
FIG. 8 is a photograph illustrating the image of the filter-paper retaining the compound of example 2 and exposed on 8 mg/L of phosgene, photographed at 365 nm.

A filter paper was cut into 2 cm×1 cm and dipped in DCM solution (1 mg/mL) containing the compound of example 2 dissolved therein. The filter paper was dried to eliminate the solvent. Then, the filter paper was placed in a sealed flask containing 0.2 mg of phenanthridine and 0.2 mg of triphosgene. The concentration of phosgene therein was 0.8 mg/L (FIG. 4) or 8 mg/L (FIG. 5). The filter paper, exposed or not exposed on 0.8 mg/L or 8 mg/L of phosgene, was photographed at 365 nm (FIGS. 6-8).

Figure 4:
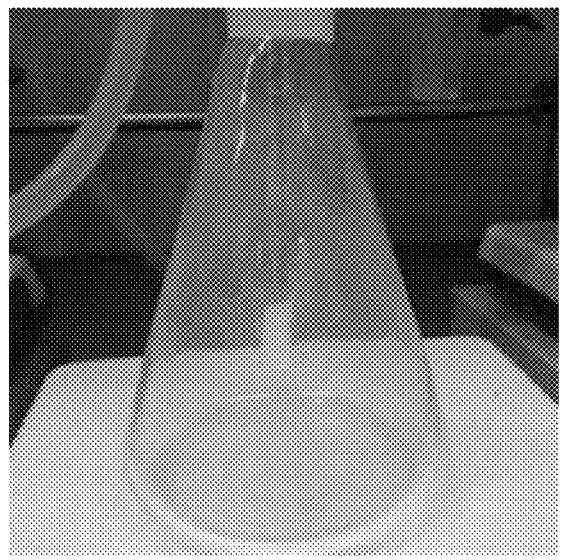
FIG. 4 is a photograph illustrating the experimental step of contacting the filter-paper retaining the compound of example 2 with 0.8 mg/L of phosgene.
Figure 5:
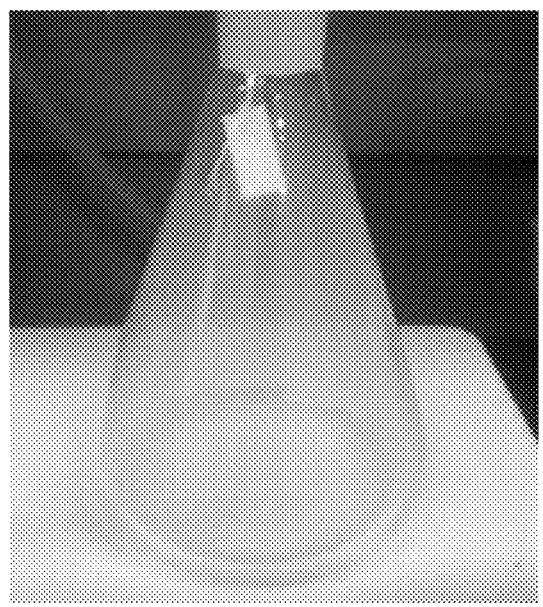
FIG. 5 is a photograph illustrating the experimental step of contacting the filter-paper retaining the compound of example 2 with 8 mg/L of phosgene.

FIG. 4 is a photograph illustrating the experimental step to contact the filter-paper retaining the compound of example 2 with 0.8 mg/L of phosgene.

FIG. 5 is a photograph illustrating the experimental step to contact the filter-paper retaining the compound of example 2 with 8 mg/L of phosgene.

Figure 6:
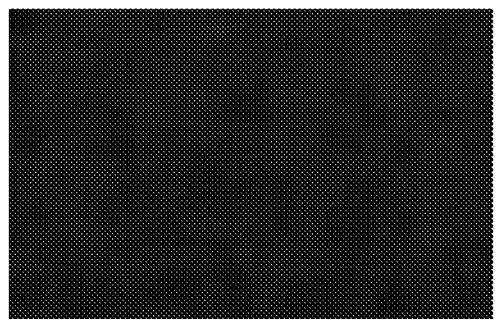
FIG. 6 is a photograph illustrating the image of the filter-paper retaining the compound of example 2 without the exposure on phosgene, photographed at 365 nm.

FIG. 6 is a photograph illustrating the image of the filter-paper retaining the compound of example 2 without the exposure on phosgene, photographed at 365 nm.

FIG. 7 is a photograph illustrating the image of the filter-paper retaining the compound of example 2 and exposed on 0.8 mg/L of phosgene, photographed at 365 nm.

FIG. 8 is a photograph illustrating the image of the filter-paper retaining the compound of example 2 and exposed on 8 mg/L of phosgene, photographed at 365 nm.

Figure 9:
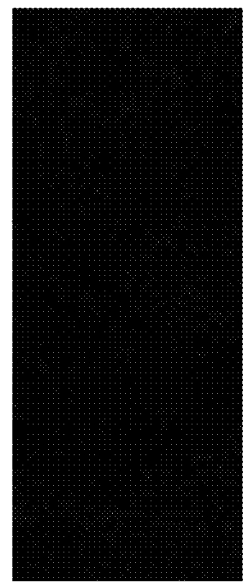
FIG. 9 is a photograph illustrating the luminescence of the glass plate coated with the compound of example 2 without the exposure on phosgene, photographed at 365 nm.

As shown in FIGS. 6-8, fluorescence properties of the filter-paper retaining the compound of example 2 exposed on phosgene were changed (FIG. 7 (fluorescence, green) and FIG. 8 (fluorescence, cyan (Stronger fluorescence than FIG. 7)), compared with the glass plate coated with the compound of example 2 not-exposed on phosgene (FIG. 9 (no fluorescence, black)).

Therefore, it was confirmed that gas-phase phosgene could be easily detected by using the compound of example 2 with the naked eye.

<Experimental Example 5> Evaluation 2 of Phosgene Detection Ability of the Compound of Example 2

The following experiment was performed to evaluate whether or not the compound of example 2 was useful for the detection of gas-phase phosgene.

The gas-phase phosgene detection ability of the compound of example 2 was evaluated by the same manner as described in example 4 except that a thin glass plate was used. The results are shown in FIGS. 9-11.

FIG. 9 is a photograph illustrating the luminescence of the glass plate coated with the compound of example 2 without the exposure on phosgene, photographed at 365 nm.

Figure 10:
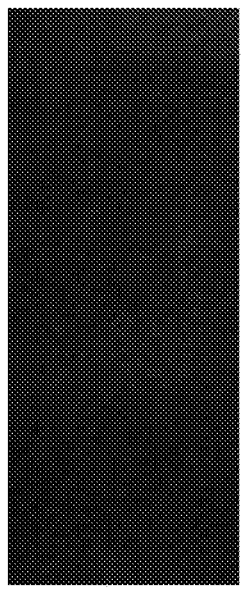
FIG. 10 is a photograph illustrating the luminescence of the glass plate coated with the compound of example 2 which was exposed on 0.8 mg/L of phosgene, photographed at 365 nm.

FIG. 10 is a photograph illustrating the luminescence of the glass plate coated with the compound of example 2 which was exposed on 0.8 mg/L of phosgene, photographed at 365 nm.

Figure 11:
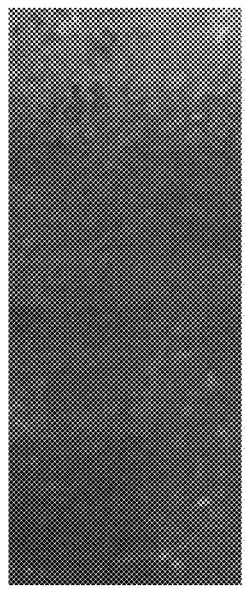
FIG. 11 is a photograph illustrating the luminescence of the glass plate coated with the compound of example 2 which was exposed on 8 mg/L of phosgene, photographed at 365 nm.

FIG. 11 is a photograph illustrating the luminescence of the glass plate coated with the compound of example 2 which was exposed on 8 mg/L of phosgene, photographed at 365 nm.

As shown in FIGS. 9-11, fluorescence properties of the glass plate coated with the compound of example 2 exposed on phosgene were changed (FIG. 10 (fluorescence, dark blue) and FIG. 11 (fluorescence, blue (Stronger fluorescence than FIG. 10)), compared with the filter-paper retaining the compound of example 2 not-exposed on phosgene (FIG. 9 (no fluorescence, black)).

Therefore, it was confirmed that the compound of example 2 of the invention is effective in detecting gas-phase phosgene by observing the changes of fluorescence properties.

<Experimental Example 6> Evaluation 3 of Phosgene Detection Ability of the Compound of Example 2

The following experiment was performed to evaluate whether or not the compound of example 2 was useful for the detection of liquid-phase phosgene.

30 μg of the compound of example was absorbed in 30 mg of silica gel, which was treated with 3 μg or 30 μg of triphosgene dissolved in chloroform. Then, the changes of fluorescence properties were observed and one of the results is presented in FIG. 12.

Figure 12:
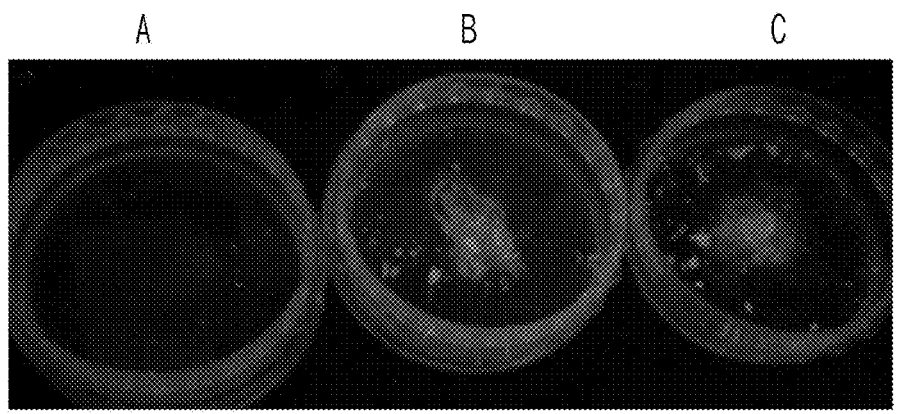
FIG. 12 is photographs illustrating the fluorescence characteristics of the silica gel containing the compound of example 2 after the treatment of 0(a), 3(b) and 30(c) μg triphosgene.

FIG. 12 is photographs illustrating the fluorescence characteristics of the silica gel containing the compound of example 2 after the treatment of 0(a), 3(b) and 30(c) μg triphosgene.

As shown in FIG. 12, fluorescence properties of the silica gel retaining the compound of example 2 treated with phosgene (b and c) were changed, compared with the silica gel retaining the compound of example 2 not-treated with phosgene (a).

Therefore, it was confirmed that the compound of example 2 of the invention is effective in detecting liquid-phase phosgene by observing the changes of fluorescence properties.

<Experimental Example 7> Evaluation 4 of Phosgene Detection Ability of the Compound of Example 2

The following experiment was performed in order to evaluate the phosgene detection ability of the compound prepared in example 2.

Particularly for the safety of the experiment, non-volatile and relatively less toxic triphosgene, the precursor of phosgene, was used instead of the volatile phosgene to evaluate the detection ability of the compound prepared in example 2. Ex wavelength=340 nm, slit width=5*3; Probe (10 um) with different equivalent of Triphosgene in p-Xylene as solvent with 1% chloroform as the co-solvent. The results are shown in FIG. 13. Each spectrum was measured at 2 min intervals.

Figure 13A:
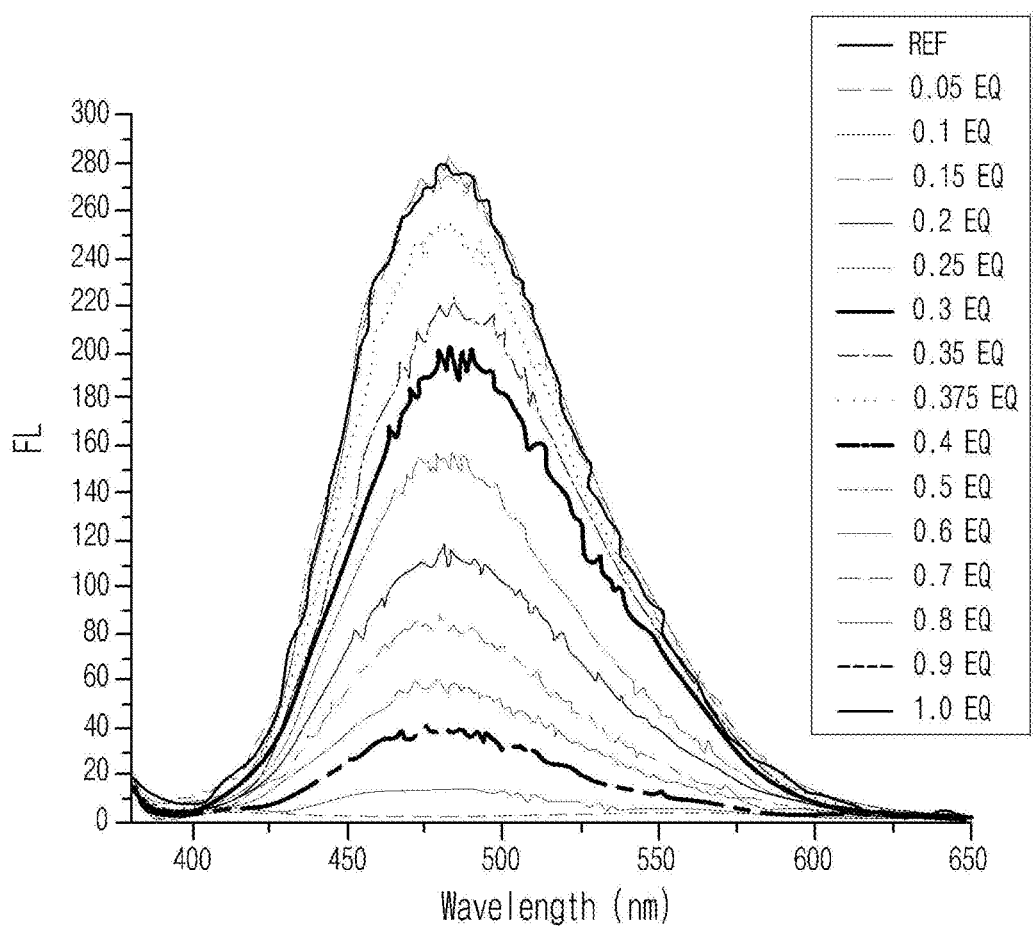
FIG. 13(a) is a graph illustrating the fluorescence spectrum of the compound of example 2 of the invention according to the concentration of phosgene.
Figure 13B:
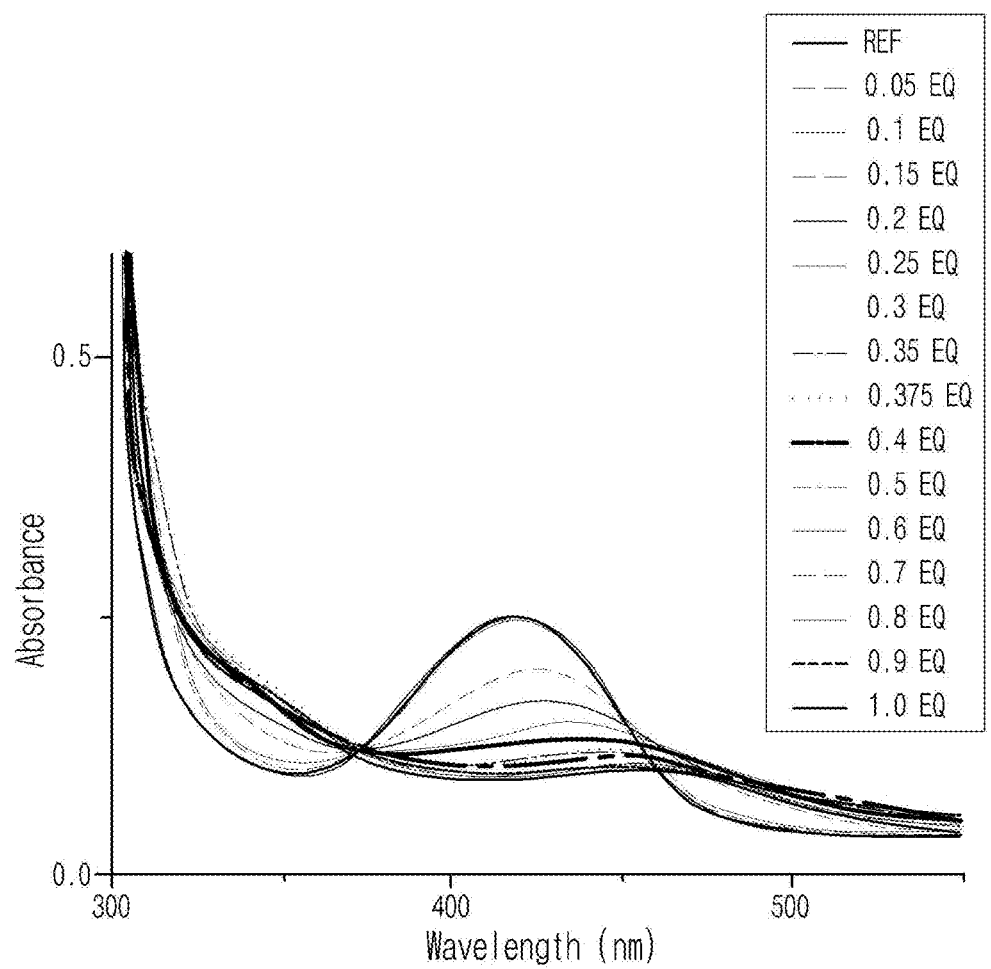
FIG. 13(b) is a graph illustrating the absorption spectrum of the compound of example 2 of the invention according to the concentration of phosgene.

FIG. 13(a) is a graph illustrating the fluorescence spectrum of the compound of example 2 of the invention according to the concentration of phosgene. FIG. 13(b) is a graph illustrating the absorption spectrum of the compound of example 2 of the invention according to the concentration of phosgene.

As shown in FIG. 13(a), the fluorescence intensity of the compound of example 2 of the invention was stronger as the concentration of phosgene was increased. As shown in FIG. 13(b), wavelength band of the absorption spectrum of the compound of example 2 of the invention was changed as the concentration of phosgene was increased.

Therefore, the compound for detecting phosgene of the present invention can be effectively used as a composition for detecting phosgene since the changes of fluorescence and color development can be observed.

In the above Experimental Examples 1-7, it was found that the compounds according to the present invention react with phosgene or DCP in a gaseous or liquid state to induce changes in fluorescence and color development at nM concentration, which induces different changes according to whether it is a phosgene or a DCP. Accordingly, the compounds of the invention or compositions containing the same may be usefully employed for phosgene and DCP detection, and can be used in the entire industry as a detection composition and a kit which are capable of selectively detecting and sensitively detecting to exposure of phosgene and DCP.

MODE FOR INVENTION

Hereinafter, the present invention is described in detail. It is to be understood, however, that the following description is provided to assist the understanding of the present invention, and the present invention is not limited thereto.

The present invention provides a compound represented by formula 1 below.

[Formula 1]

wherein
A is

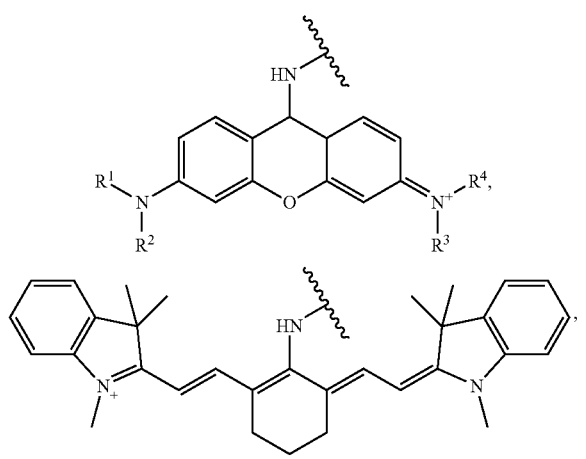

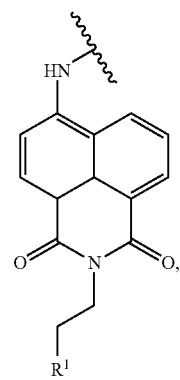

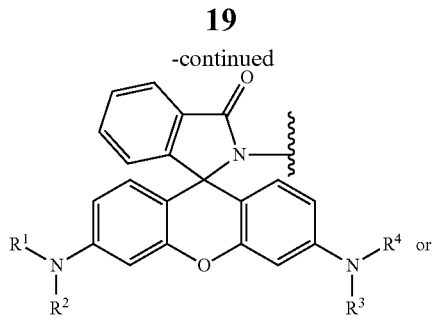

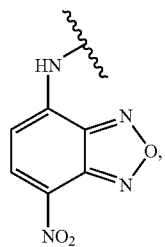

R1 is —H, C1-10 straight or branched alkyl, C1-10 straight or branched alkoxy, or 4-7 membered heterocycloalkyl containing 1-3 hetero atoms selected from the group consisting of N, O, and S; and R2, R3 and R4 is independently —H, C1-10 straight or branched alkyl, or C1-10 straight or branched alkoxy.

Preferably, R1 is —H, C1-5 straight or branched alkyl, C1-5 straight or branched alkoxy, or 4-6 membered heterocycloalkyl containing 2-3 hetero atoms selected from the group consisting of N, O, and S.

More preferably, R1 is C1-4 straight or branched alkyl, or 6 membered heterocycloalkyl containing 2-3 hetero atoms selected from the group consisting of N, O, and S.

Most preferably, the compound represented by formula 1 above is the compound selected from the group consisting of the following compounds.

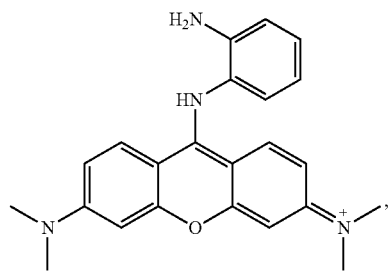

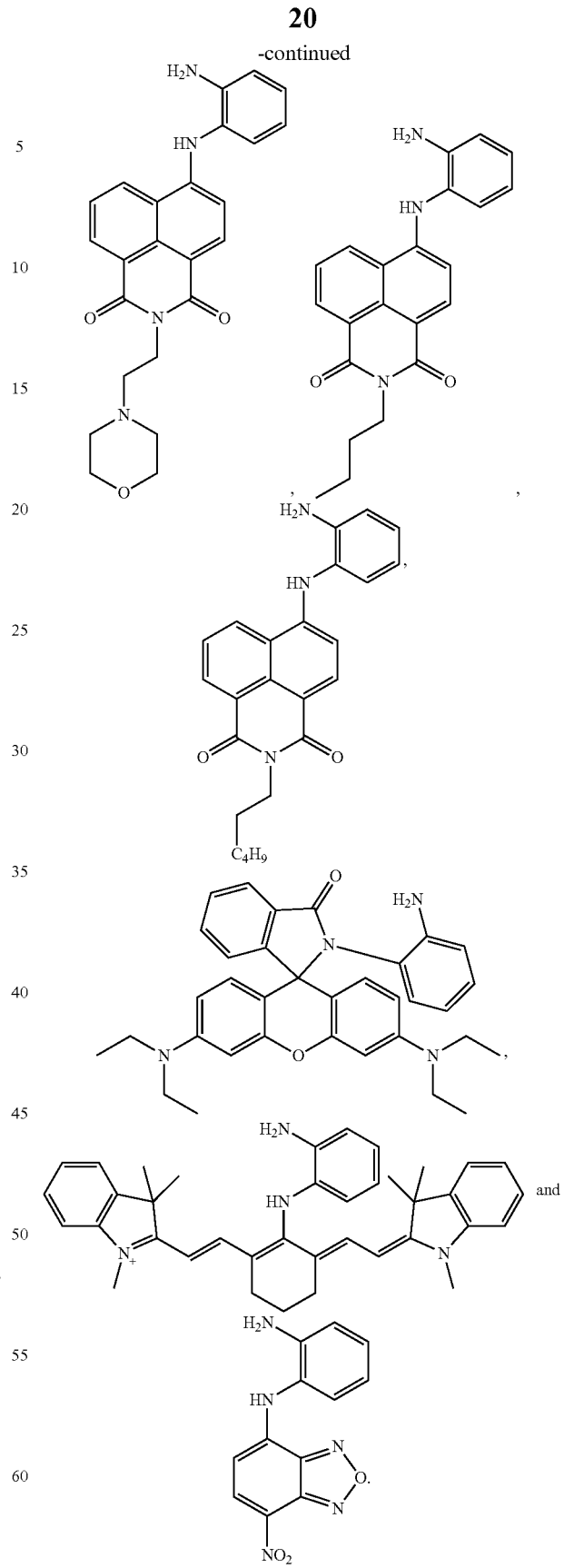

The present invention also provides a method for preparing the compound represented by formula 1 containing the step of reacting the compound represented by A-LG with the compound represented by formula 2 to give the compound represented by formula 1 (step 1) as shown in the below reaction formula 1.

[Reaction Formula 1]

Step 1

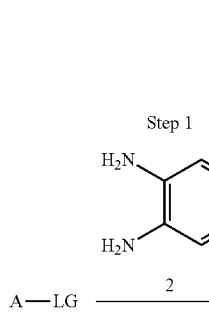

In the reaction formula 1, A is as defined in formula 1; and LG is =O, =S or halogene.

Hereinafter, the method for preparing the compound represented by formula 1 of the present invention is described in more detail step by step.

In the method for preparing the compound represented by formula 1 of the invention, step 1 is to give the compound represented by formula 1 by reacting the compound represented by A-LG with the compound represented by formula 2.

At this time, the compound represented by formula 1 is prepared by the method shown in reaction formula 2, reaction formula 3, reaction formula 4, reaction formula 5, or reaction formula 6.

[Reaction Formula 2]

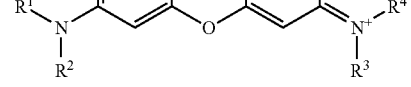

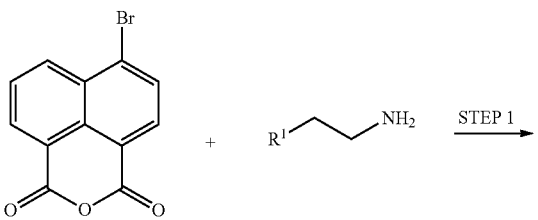

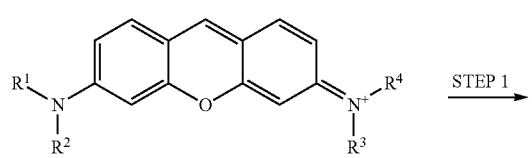

[Reaction Formula 3]

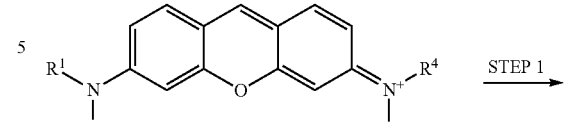

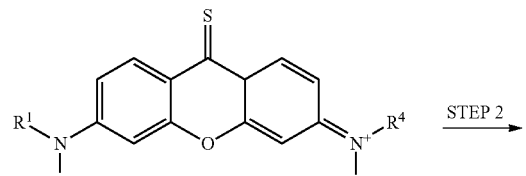

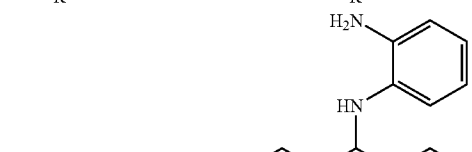

[Reaction Formula 4]

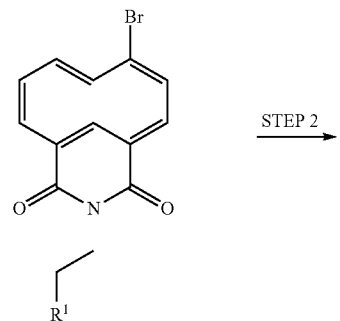

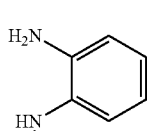

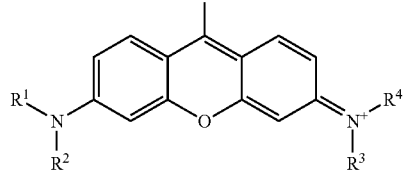

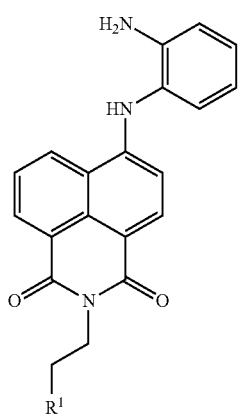

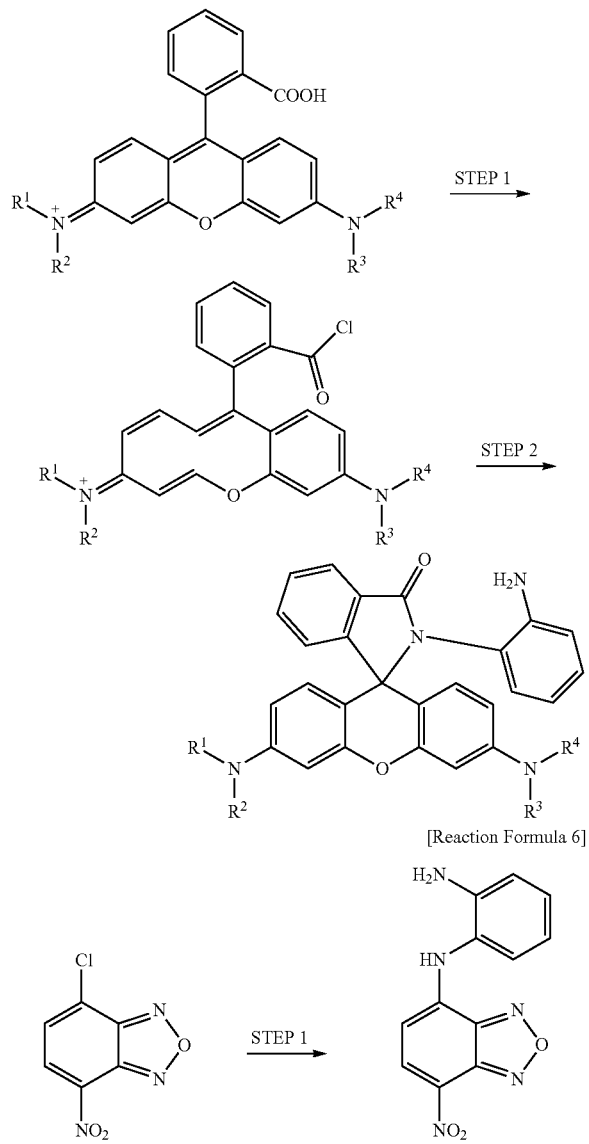

[Reaction Formula 5]

[Reaction Formula 6]

Further, the present invention provides a composition for detecting phosgene or DCP (diethyl chlorophosphate) comprising the compound represented by formula 1.

The present invention also provides a kit for the detection of one or more compounds selected from the group consisting of phosgene and DCP (diethyl chlorophosphate) comprising the compound represented by formula 1.

Herein, the detection is preferably performed by observing the changes of fluorescence or absorbance caused by the changes of π-conjugation system resulted from the nucleophilic attack of phenylenediamine included in the compound against phosgene or DCP (diethyl chlorophosphate).

The present invention also provides a method for the detection of one or more compounds selected from the group consisting of phosgene and DCP (diethyl chlorophosphate) comprising the following steps:

contacting the detection kit of the invention with the sample to be analyzed (step 1); and evaluating the changes of fluorescence or absorption properties of the compound represented by formula 1 included in the detection kit after the contact of step 1 (step 2).

Hereinafter, the method for the detection of one or more compounds selected from the group consisting of phosgene and DCP (diethyl chlorophosphate) of the present invention is described in more detail step by step.

In the method for the detection of one or more compounds selected from the group consisting of phosgene and DCP (diethyl chlorophosphate) of the present invention, step 1 is to contact the detection kit with the sample to be analyzed.

At this time, the sample herein is in the solid, liquid, or gas-phase, and more preferably in the liquid or gas-phase. The sample herein may include or not include phosgene or DCP (diethyl chlorophosphate), which is the detection target of this invention.

In the method for the detection of one or more compounds selected from the group consisting of phosgene and DCP (diethyl chlorophosphate) of the present invention, step 2 is to evaluate the changes of fluorescence or absorption properties of the compound represented by formula 1 included in the detection kit after the contact of step 1.

Herein, when the sample contains phosgene or DCP (diethyl chlorophosphate), the detection target, the changes of fluorescence or absorption properties of the compound represented by formula 1 included in the detection kit can be observed.

Another experiment was also performed to investigate whether or not the fluorescence or absorption properties were changed when the compound of example 1 of the invention was contacted with liquid-phase phosgene or DCP (diethyl chlorophosphate).

As a result, it was confirmed that when the compound of example 1 of the invention was contacted with phosgene or DCP (diethyl chlorophosphate), the fluorescence or absorption properties were significantly changed so that they could be observed even with the naked eye (see FIGS. 1 and 2 of Experimental Examples 1 and 2). Another experiment was also performed to investigate whether or not the fluorescence or absorption properties were changed when the compound of example 1 of the invention was contacted with gas-phase phosgene or DCP (diethyl chlorophosphate).

As a result, it was confirmed that when the compound of example 1 of the invention was contacted with phosgene or DCP (diethyl chlorophosphate), the fluorescence or absorption properties were significantly changed so that they could be observed even with the naked eye (see FIG. 3 of Experimental Example 3).

Further, an experiment was performed to evaluate whether or not the compound of example 2 of the invention was effective in detecting gas-phase phosgene. As a result, it was confirmed that the compound of example 2 was significantly effective in detecting gas-phase phosgene even with the naked eye (see FIGS. 4~11 of Experimental Examples 4 and 5).

In addition, an experiment was performed to evaluate whether or not the compound of example 2 of the invention was effective in detecting liquid-phase phosgene. As a result, it was confirmed that the compound of example 2 was significantly effective in detecting liquid-phase phosgene by observing the changes of fluorescence properties (see FIG. 12 of Experimental Example 6).

Therefore, the compound of the present invention forms a different bond with phosgene or DCP to cause a change in the pi-conjugated system of the binding molecule, and the fluorescence and the color change according to the phosgene or DCP are different from each other. The compound has the effect of selectively detecting phosgene or DCP, respectively, or by mixing them.

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparative Example 1> Preparation of o-phenylenediamine-pyronin (N-(9-(2-aminophenylamino)-6-(dimethylamino)-3H-xanthen-3-ylidene)-N-methylmethanaminium)

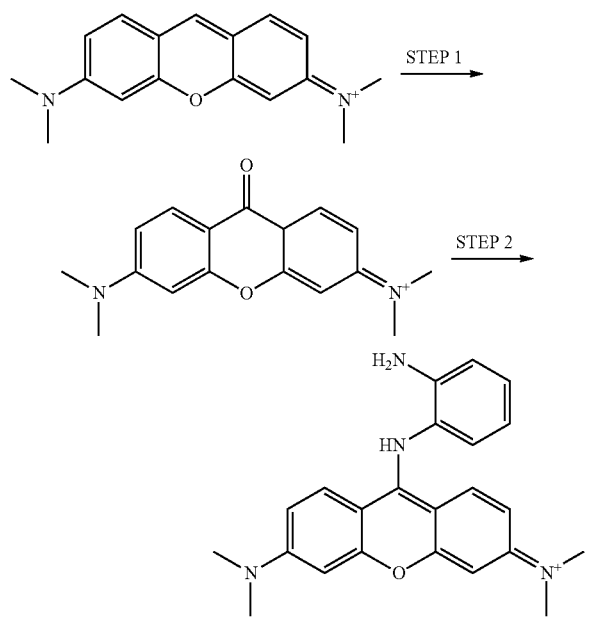

Step 1: Preparation of N-(6-(dimethylamino)-9-oxo-9,9a-dihydroxandene-3-ylidene)-N-methylmethanaminium N-(6-(dimethylamino)-3H-xandene-3-ylidene)-N-methylmethanaminium was reacted with KCN for 18 hours, reacted with FeCl3/HCl for 12 hours, and then reacted with NaHCO$_3$, resulting in the preparation of N-(6-(dimethylamino)-9-oxo-9,9a-dihydroxandene-3-ylidene)-N-methylmethanaminium.

Step 2: Preparation of N-(9-(2-aminophenylamino)-6-(dimethylamino)-3H-xanthen-3-ylidene)-N-methylmethanaminium The compound prepared in step 1 above was reacted with Tf2O and then reacted with benzene-1,2-diamine to give N-(9-(2-aminophenylamino)-6-(dimethylamino)-3H-xanthen-3-ylidene)-N-methylmethanaminium (yield: 40%).

<Example 1> Preparation of Compounds for Detecting Phosgene and DCP 1

Step 1: Preparation of N-(6-(dimethylamino)-9-thioxo-9,9a-dihydroxandene-3-ylidene)-N-methylmethanaminium

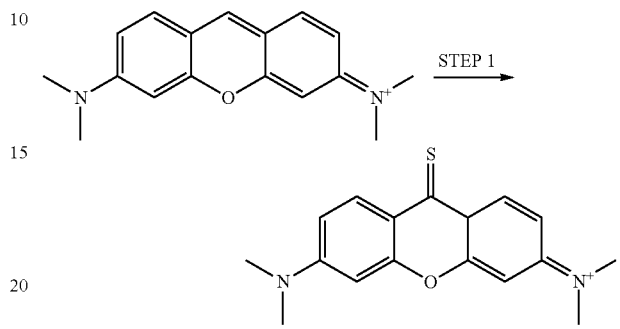

THF (40 ml) containing t-BuOK (0.56 g, 3 eq) was added to the solution containing Pyronine Y (N-(6-(dimethylamino)-3H-xandene-3-ylidene)-N-methylmethanaminium) (0.5 g, 1.65 m mol) and sulfur (0.79 g, 15 eq). The reaction mixture was refluxed for 10 hours. Termination of the reaction was confirmed by TLC. Then, the reaction mixture was cooled down at room temperature and filtered. Silica gel column chromatography was performed with the residue (eluent, PE:DCM, 1:1) to give the target compound as a yellow solid (yield: 50%).

1H NMR (300 MHz, CDCl3), δ: 8.70 (d, J=9.2 Hz, 2H), 6.75 (dd, J=9.2, 2.3 Hz, 2H), 6.43 (d, J=2.3 Hz, 2H), 3.13 (s, 12H). 13C NMR (75 MHz, CDCl3), δ: 196.26, 154.58, 153.03, 131.80, 120.07, 110.52, 96.06, 40.24. ESI-MS: Calcd. for 299.11; Found 299.20.

Step 2: Preparation of N-(9-(2-aminophenylamino)-6-(dimethylamino)-3H-xanthen-3-ylidene)-N-methylmethanaminium

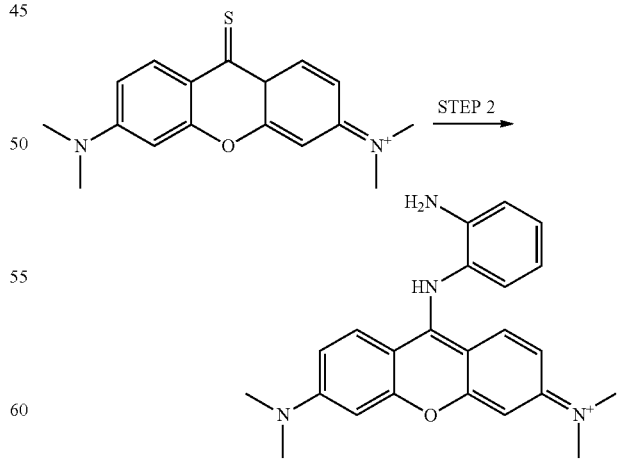

90 μl (2 eq) of Tf2O was added drop by drop to the anhydrous CH2Cl2 solution (10 ml) containing 80 mg (0.268 m mol) of the compound prepared in step 1 above dissolved therein. The reaction mixture was well mixed with stirring at room temperature for 10 minutes. 0.29 g (10 eq) of o-phenylenediamine solution was added to the reaction mixture above, followed by stirring for 10 more hours. Then, CH2Cl2 was eliminated under reduced pressure. The solid residue was purified by silica gel chromatography (eluent, EA:DCM, 1:2) to give the target compound as a yellow solid (yield: 80%).

1H NMR (300 MHz, MeOD), δ: 7.78 (d, J=9.5 Hz, 2H), 7.25 (m, 1H), 7.09 (dd, J=7.8, 1.4 Hz, 1H), 6.96 (dd, J=7.8, 1.4 Hz, 1H), 6.81 (dd, J=3.9, 1.9 Hz, 1H), 6.76 (m, 2H), 6.71 (d, J=2.5 Hz, 2H), 3.18 (s, 12H). 13C NMR (75 MHz, MeOD), δ: 157.01, 155.46, 154.03, 147.21, 143.91, 129.31, 126.98, 126.52, 117.72, 116.26, 110.67, 102.83, 96.68, 38.80. ESI-MS: [M]+Calcd. for 372.20; Found 372.30.

<Example 2> Preparation of Compounds for Detecting Phosgene and DCP 2

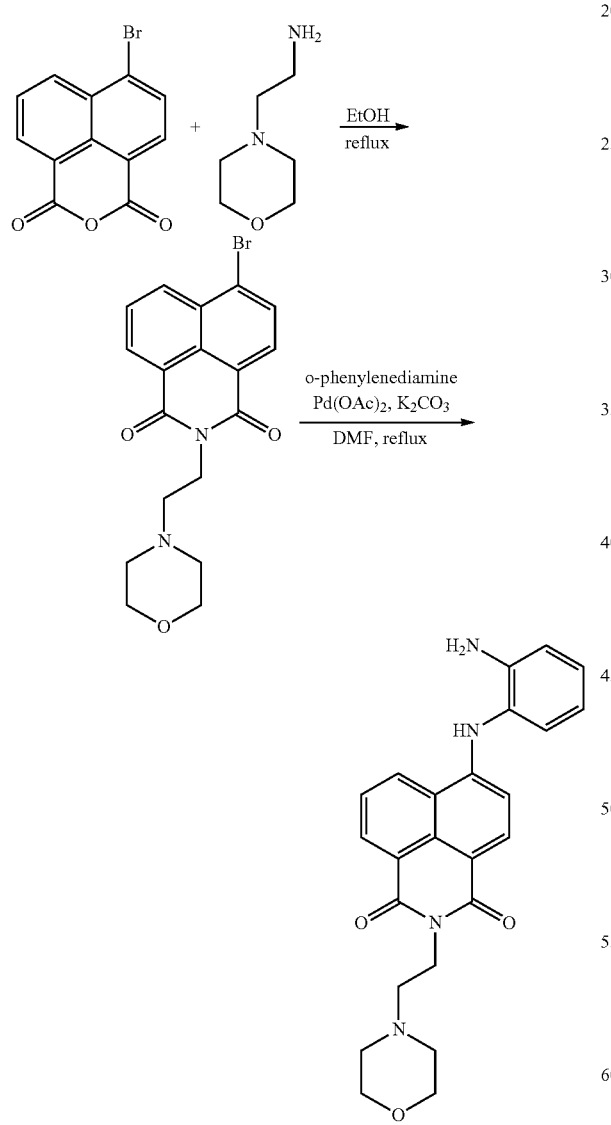

To a solution of 4-bromo-1,8-naphthalene anhydride (1.38 g, 5.0 mmol) in anhydrous EtOH (20.0 ml) at room temperature was added 4-(2-aminoethyl)morpholine (715 mg, 5.5 mmol). After refluxing for 4 h, the reaction mixture was cooled and filtered to give 4-bromine-1,8-naphthalimide. This naphthalimide (389 mg, 1.0 mmol) and o-phenylenediamine (540 mg, 5.0 mmol) were dissolved in anhydrous DMF (20 mL), Subsequently, K2CO3 (550 mg, 4 mmol) and Pd(OAc) (44 mg, 2 mmol) was added under nitrogen. The reaction was then refluxed overnight. The solvent DMF was then removed under vacuum. The crude product was treated with water, extracted with dichloromethane and dried over anhydrous MgSO4. The organic layer was removed and the residue was purified by column chromatography to give 0.18 g of product (yellow solid, 43%).

1H NMR (CDCl3, 300 MHz) δ (ppm)=8.59 (m, 1H), 8.35 (d, 1H), 8.28 (d, 1H), 7.69 (m, 1H), 7.17 (m, 2H), 6.92-6.77 (m, 2H), 6.67 (d, 1H), 6.53 (s, 1H), 4.37-4.23 (m, 2H), 3.79 (s, 2H), 3.71-3.88 (m, 4H), 2.72-2.61, 2H), 2.57 (s, 4H). 13C NMR (75 MHz, CDCl3) δ=164.51, 163.89, 147.49, 142.82, 133.96, 131.31, 128.32, 127.44, 126.22, 125.32, 124.50, 123.21, 120.74, 119.50, 116.75, 112.30, 107.75, 67.02, 56.23, 53.80, 36.98. HRMS (ESI) m/z=417.1718 [M+H]+, calcd for C24H25N4O3=417.1927.

<Example 3> Preparation of Compounds for Detecting Phosgene and DCP 3

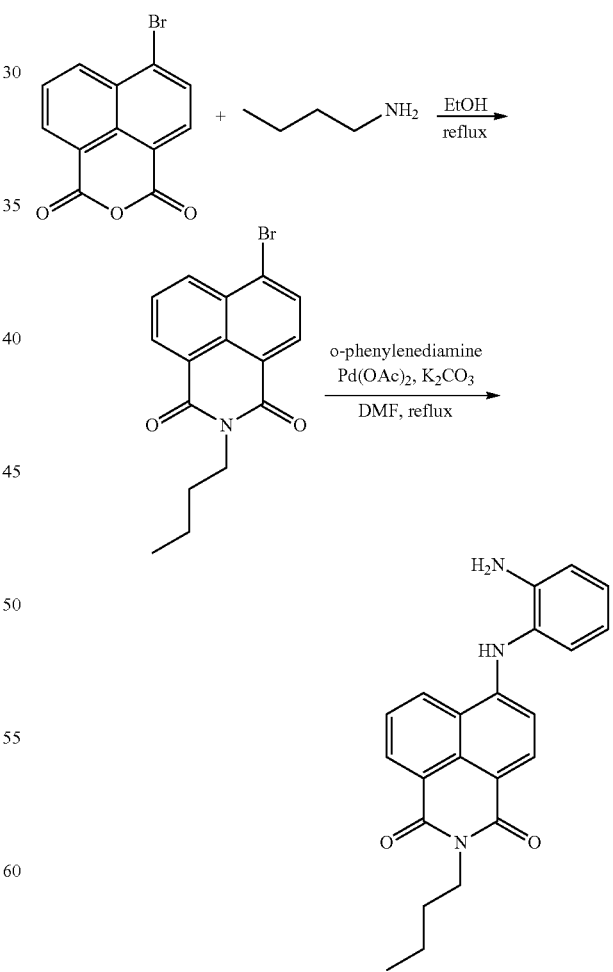

To a solution of 4-bromo-1,8-naphthalene anhydride (1.38 g, 5.0 mmol) in anhydrous EtOH (20.0 ml) was added butylamine (480 mg, 5.5 mmol) at room temperature. After refluxing for 4 h, the reaction mixture was cooled and filtered to give 4-bromine-1, 8-naphthalimide. This naphthalimide (540 mg, 5.0 mmol) and o-phenylenediamine (540 mg, 5.0 mmol) were dissolved in anhydrous DMF (20 mL), Subsequently, K2CO3 (550 mg, 4 mmol) and Pd(OAc) (44 mg, 2 mmol) under nitrogen. The reaction was then refluxed overnight. The solvent DMF was then removed under vacuum. The crude product was treated with water, extracted with dichloromethane and dried over anhydrous MgSO4. The organic layer was removed and the residue was purified by column chromatography to give 0.11 g of product (yellow solid, 61%).

1H NMR (DMSO-d6, 300 MHz) δ (ppm)=9.01 (s, 1H), 8.91-8.88 (m, 1H), 8.50-8.47 (m, 1H), 8.20 (d, J=8.6 Hz, 1H), 7.78-7.73 (m, 1H), 7.09 (t, J=7.2 Hz, 2H), 6.88-6.84 (m, 1H), 6.69-6.63 (m, 1H), 6.41 (d, J=8.5 Hz, 1H), 5.04 (s, 2H), 4.16-3.89 (m, 2H), 1.58 (d, J=7.5 Hz, 2H), 1.47-1.19 (m, 2H), 0.92 (t, J=7.3 Hz, 3H); 13C NMR DMSO-d6, δ=164.47, 163.63, 150.48, 145.65, 134.54, 131.47, 130.23, 130.05, 128.82, 128.44, 125.14, 123.99, 122.55, 121.34, 117.19, 116.35, 109.79, 107.01, 55.61, 30.53, 20.51, 14.46. HRMS (ESI) m/z=360.1706 [M+H]+, calcd for C24H25N4O3=360.1712.

<Example 4> Preparation of Compounds for Detecting Phosgene and DCP 4

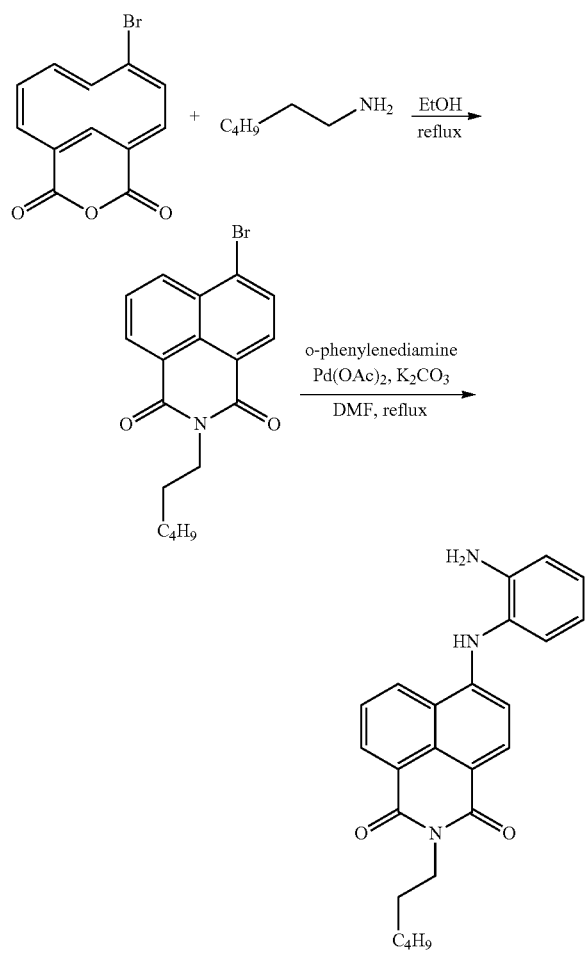

The target compound was prepared by conducting the same synthesis as in Example 3 except that hexylamine was used instead of the butylamine used in Example 3.

<Example 5> Preparation of Compounds for Detecting Phosgene and DCP 5

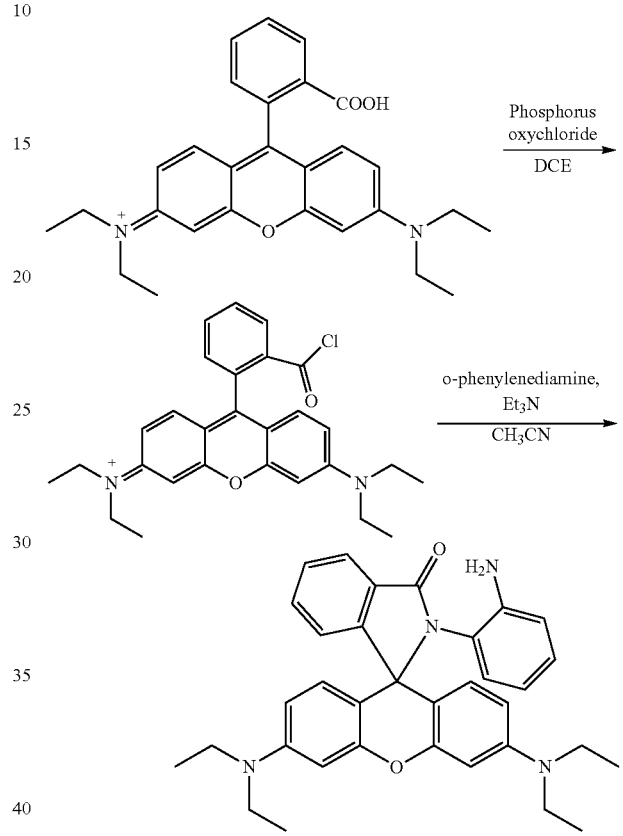

To a solution of rhodamine B base (1.01 g, 2.3 mmol) in dry 1,2-dichloroethane (8.0 mL) at room temperature was added phosphorus oxychloride (6.9 mmol) over a period of 5 min. After being stirred at reflux for 4 h, the mixture was cooled and concentrated under vacuum to give the crude rhodamine B acid chloride. A solution of the acid chloride in dry acetonitrile (10 mL) was added dropwise to a solution of o-diaminobenzene (14 mmol) in dry acetonitrile (6.0 mL) containing triethylamine (8.0 mL). After being stirred for 4 h at room temperature, the mixture was concentrated under vacuum, and the residue was subjected to column chromatography to give target compound as a white solid in 83% yield.

1H NMR (CDCl3, 300 MHz) δ (ppm): 8.03-8.05 (m, 1H); 7.53-7.60 (m, 2H); 7.25-7.27 (m, 1H); 6.94-6.99 (m, 1H); 6.68 (d, J=8.7 Hz, 2H); 6.58 (dd, J=7.8 Hz, J=1.2 Hz, 1H); 6.40-6.46 (m, 1H); 6.31 (d, J=8.7 Hz, 2H); 6.28 (b, 2H); 6.10 (dd, J=8.1 Hz, J=1.5 Hz, 1H); 3.44 (s, 2H); 3.35 (q, J=6.9 Hz, 8H); 1.16 (t, J=7.2 Hz, 12H). 13C NMR (CDCl3, 75 MHz) δ (ppm): 166.63, 161.22, 154.20, 152.66, 149.15, 144.75, 132.81, 129.03, 128.97, 128.85, 128.55, 124.51, 123.66, 122.46, 118.43, 117.23, 108.21, 98.28, 68.27, 44.60, 31.15, 12.76. HRMS (ESI) m/z calcd for C34H36N4O2 [M+H]+ 533.2565. Found 533.2838.

<Example 6> Preparation of Compounds for Detecting Phosgene and DCP 6

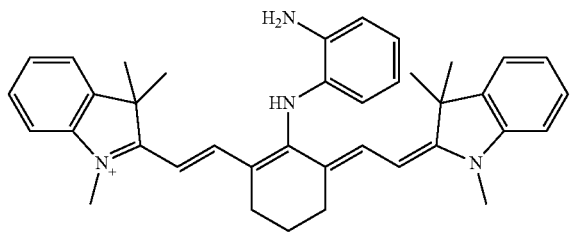 [SMILES: CN1/C(=C/C=C2\CCCC(/C=C/C3=[N+](C)c4ccccc4C3(C)C)=C2Nc2ccccc2N)C(C)(C)c2ccccc21]

The target compound was prepared by carrying out the same synthesis as in Example 1 except that

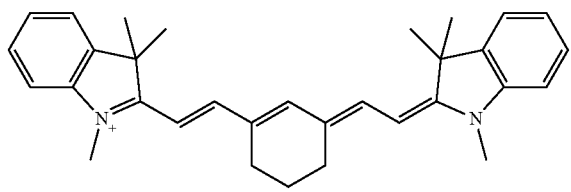

was used instead of

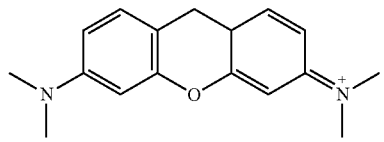

in the step 1 of Example 1 above.

<Example 7> Preparation of Compounds for Detecting Phosgene and DCP 7

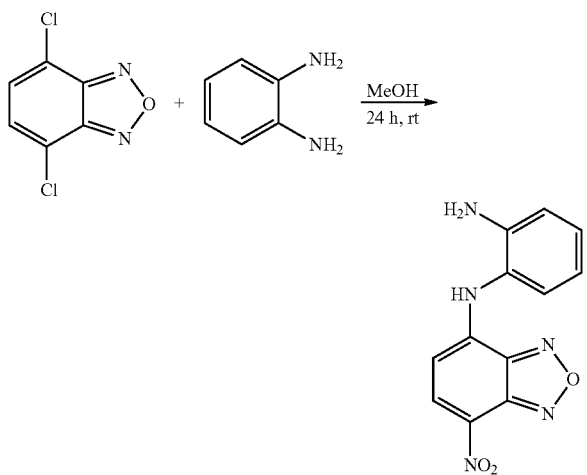

To a solution of o-phenylenediamine (0.32 g, 3.0 mmol) in methanol (10 mL) was added NBD-Cl (0.20 g, 1.0 mmol) in methanol (10 mL) at room temperature with stirring. The resulting mixture was stirred at room temperature for 24 hours. Filtered and washed several times with methanol to give a target compound (reddish brown solid, 71%).

1H NMR (DMSO-d6, 300 MHz): δ 10.69 (brs, 1H), 8.54 (d, J=8.7 Hz, 1H), 7.09-7.15 (m, 2H), 6.84 (d, J=7.2 Hz, 1H), 6.64 (t, J=7.8 Hz, 1H), 5.93 (d, J=8.7 Hz, 1H), 5.27 (brs, 2H). 13C NMR (DMSO-d6, 75 MHz): d 145.49, 145.04, 144.96, 144.92, 138.58, 129.44, 128.14, 121.95, 116.77, 116.49, 113.59, 102.34. HRMS (EI) m/z=270.0640 [M]+, calcd for C12H9N5O3=270.0704.

<Comparative Example 1> Preparation of N-(9-(4-aminophenylamino)-6-(dimethylamino)-9,9a-dihydroxandene-3-ylidene)-N-methylmethanaminium

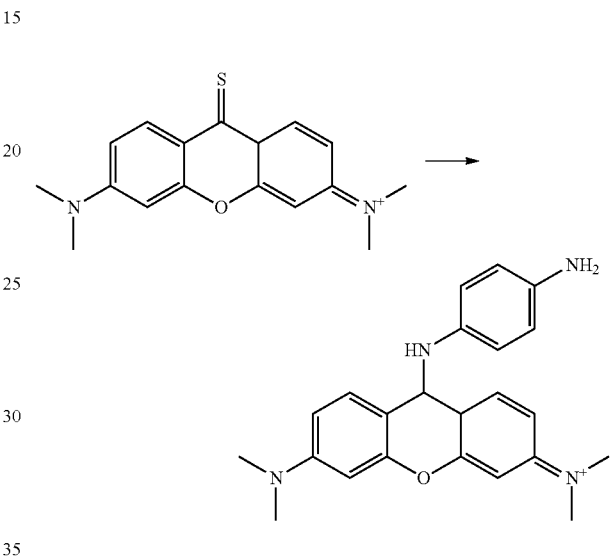

50 mg (0.168 m mol) of the compound prepared in step 1 of example 1 was dissolved in CH2Cl2 (10 ml), to which 57 μl (2 eq) of Tf2O was added drop by drop. The reaction mixture was stirred for 10 minutes, to which 235 μl (15 eq) of phenylamine was added. The mixture was stirred at room temperature for overnight. Upon completion of the reaction, CH2Cl2 was eliminated under reduced pressure. The solid residue was purified by silica gel chromatography (eluent, EA:DCM, 1:3) to give the target compound as an orange solid (yield: 70%).

1H NMR (300 MHz, MeOD), δ: 7.67 (d, J=9.5 Hz, 2H), 7.56 (dd, J=7.7, 6.6 Hz, 2H), 7.46 (m, 1H), 7.40 (d, J=7.7 Hz, 2H), 6.80 (dd, J=9.5, 2.4 Hz, 2H), 6.73 (d, J=2.4 Hz, 2H), 3.19 (s, 12H). 13C NMR (75 MHz, MeOD), δ: 157.34, 155.65, 153.33, 140.66, 129.94, 127.66, 127.16, 125.05, 110.83, 102.73, 96.32, 38.86. ESI-MS: [M]+Calcd for 358.19; Found 358.30.

<Comparative Example 2> Preparation of N-(6-(dimethylamino)-9-(phenylamino)-9,9a-dihydroxandene-3-ylidene)-N-methylmethanaminium

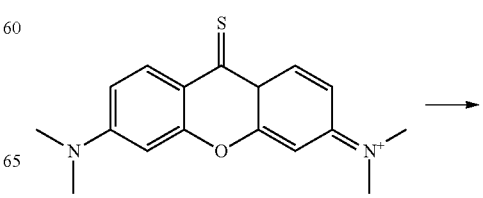

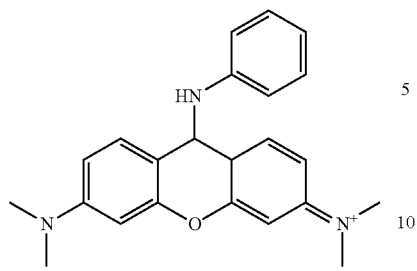

100 mg (0.336 m mol) of the compound prepared in step 1 of example 1 was dissolved in CH2Cl2 (15 ml), to which 114 μl (2 eq) of Tf2O was added drop by drop. The reaction mixture was stirred for 10 minutes, to which 0.54 g (15 eq) of p-phenylenediamine was added. The mixture was stirred at room temperature for overnight. Upon completion of the reaction, the solvent was eliminated under reduced pressure. The solid residue was purified by silica gel chromatography (eluent, DCM:EtOH, 30:1) to give the target compound as a yellow solid (yield: 70%).

1H NMR (300 MHz, MeOD) δ 7.74 (s, 2H), 7.13 (m, 2H), 6.84 (m, 4H), 6.70 (d, J=2.5 Hz, 2H), 3.18 (s, 12H). 13C NMR (75 MHz, MeOD) δ 157.01, 154.99, 150.34, 129.75, 128.51, 127.92, 116.80, 112.16, 103.60, 97.75, 40.26. [M]+ calcd for 373.20, Found 373.30.

The chemical formulae of the compounds prepared in examples 1~7 are shown in Table 1.

TABLE 1-continued

| Example | Chemical Formula |
|---------|------------------|
| 7 | 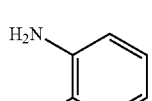 |

<Experimental Example 1> Evaluation of Phosgene Detection Ability of the Compound of Example 1

The following experiment was performed in order to evaluate the phosgene detection ability of the compound prepared in example 1.

Particularly for the safety of the experiment, non-volatile and relatively less toxic triphosgene, the precursor of phosgene, was used instead of the volatile phosgene to evaluate the detection ability of the compound prepared in example 1. The compound of example 1 was loaded in chloroform at the concentration of 10 μM, to which triphosgene was added with different concentrations (0-2 eq), during which the changes of fluorescence and absorbance were observed to evaluate the phosgene detection ability. The results are shown in FIG. 1. In the experiment, excitation wavelength was 580 nm and slit width was 1.5 nm. Each spectrum was measured at 2 min intervals.

FIG. 1(a) is a graph illustrating the fluorescence spectrum of the compound of example 1 of the invention according to the concentration of phosgene, wherein the fluorescence photograph is on the right side of the graph. FIG. 1(b) is a graph illustrating the absorption spectrum of the compound of example 1 of the invention according to the concentration of phosgene, wherein the color development photograph is on the right side of the graph.

As shown in FIG. 1(a), the fluorescence intensity of the compound of example 1 of the invention was stronger as the concentration of phosgene was increased, and thus red fluorescence was observed with the naked eye. As shown in FIG. 1(b), wavelength band of the absorption spectrum of the compound of example 1 of the invention was changed as the concentration of phosgene was increased. The color thereof started yellow and turned purple, which was also observed with the naked eye.

Therefore, the compound for detecting phosgene of the present invention can be effectively used as a composition for detecting phosgene since the changes of fluorescence and color development can be observed with the naked eye.

<Experimental Example 2> Evaluation of DCP (Diethyl Chlorophosphate) Detection Ability of the Compound of Example 1

The following experiment was performed by the same manner as described in experimental example 1 in order to evaluate the DCP detection ability of the compound prepared in example 1 of the invention except that DCP (diethyl chlorophosphate) was used instead of phosgene. The results are shown in FIG. 2.

FIG. 2(a) is a graph illustrating the fluorescence spectrum of the compound of example 1 of the invention according to the concentration of DCP (diethyl chlorophosphate), wherein the fluorescence photograph is on the right side of the graph.

FIG. 2(b) is a graph illustrating the absorption spectrum of the compound of example 1 of the invention according to the concentration of DCP (diethyl chlorophosphate).

As shown in FIG. 2(a), the fluorescence intensity of the compound of example 1 of the invention was stronger as the concentration of DCP (diethyl chlorophosphate) was increased, and thus green fluorescence was observed with the naked eye.

As shown in FIG. 2(b), wavelength band of the absorption spectrum of the compound of example 1 of the invention was changed as the concentration of DCP (diethyl chlorophosphate) was increased.

Therefore, the compound for the detection of DCP (diethyl chlorophosphate) of the present invention can be effectively used as a composition for the detection of DCP (diethyl chlorophosphate) since the changes of fluorescence and color development can be observed with the naked eye.

<Experimental Example 3> Evaluation of Gas-Phase Phosgene and DCP (Diethyl Chlorophosphate) Detection Ability of the Compound of Example 1

The following experiment was performed in order to evaluate the gas-phase phosgene and DCP detection ability of the compound of example 1 of the invention.

Particularly, in order to evaluate whether or not the compound prepared in example 1 could act as a real sensor to detect gas-phase phosgene and DPC efficiently, a kit was constructed wherein the compound of example 1 was fixed on polyethylene oxide film. The kit was exposed on different concentrations of phosgene and DCP (0-20 ppm), followed by observation of the changes of fluorescence and color development in the compound of example 1. The results are shown in FIG. 3.

FIG. 3(a) is an image illustrating the changes of fluorescence resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of fluorescence.

FIG. 3(b) is an image illustrating the changes of color development resulted from the exposure on gas-phase phosgene or gas-phase DCP (diethyl chlorophosphate). Precisely, the compound of example 1 was prepared as a sensor which was exposed on gas-phase phosgene or gas-phase DCP, followed by observation of the changes of color development.

As shown in FIG. 3, the compound of the example of the present invention can be useful as a sensor to detect the changes of fluorescence and color development according to the exposure on gas-phase phosgene and DCP (diethyl chlorophosphate).

<Experimental Example 4> Evaluation 1 of Phosgene Detection Ability of the Compound of Example 2

The following experiment was performed to evaluate whether or not the compound of example 2 was useful for the detection of gas-phase phosgene.

A filter paper was cut into 2 cm×1 cm and dipped in DCM solution (1 mg/mL) containing the compound of example 2 dissolved therein. The filter paper was dried to eliminate the solvent. Then, the filter paper was placed in a sealed flask containing 0.2 mg of phenanthridine and 0.2 mg of triphosgene. The concentration of phosgene therein was 0.8 mg/L (FIG. 4) or 8 mg/L (FIG. 5). The filter paper, exposed or not exposed on 0.8 mg/L or 8 mg/L of phosgene, was photographed at 365 nm (FIGS. 6-8).

FIG. 4 is a photograph illustrating the experimental step to contact the filter-paper retaining the compound of example 2 with 0.8 mg/L of phosgene.

FIG. 5 is a photograph illustrating the experimental step to contact the filter-paper retaining the compound of example 2 with 8 mg/L of phosgene.

FIG. 6 is a photograph illustrating the image of the filter-paper retaining the compound of example 2 without the exposure on phosgene, photographed at 365 nm.

FIG. 7 is a photograph illustrating the image of the filter-paper retaining the compound of example 2 and exposed on 0.8 mg/L of phosgene, photographed at 365 nm.

FIG. 8 is a photograph illustrating the image of the filter-paper retaining the compound of example 2 and exposed on 8 mg/L of phosgene, photographed at 365 nm.

As shown in FIGS. 6~8, color of the filter-paper retaining the compound of example 2 exposed on phosgene was changed, compared with the filter-paper retaining the compound of example 2 not-exposed on phosgene.

Therefore, it was confirmed that gas-phase phosgene could be easily detected by using the compound of example 2 with the naked eye.

<Experimental Example 5> Evaluation 2 of Phosgene Detection Ability of the Compound of Example 2

The following experiment was performed to evaluate whether or not the compound of example 2 was useful for the detection of gas-phase phosgene.

The gas-phase phosgene detection ability of the compound of example 2 was evaluated by the same manner as described in example 4 except that a thin glass plate was used. The results are shown in FIGS. 9~11.

FIG. 9 is a photograph illustrating the luminescence of the glass plate coated with the compound of example 2 without the exposure on phosgene.

FIG. 10 is a photograph illustrating the luminescence of the glass plate coated with the compound of example 2 which was exposed on 0.8 mg/L of phosgene.

FIG. 11 is a photograph illustrating the luminescence of the glass plate coated with the compound of example 2 which was exposed on 8 mg/L of phosgene.

As shown in FIGS. 9~11, fluorescence properties of the glass plate coated with the compound of example 2 exposed on phosgene were changed, compared with the glass plate coated with the compound of example 2 not-exposed on phosgene.

Therefore, it was confirmed that the compound of example 2 of the invention is effective in detecting gas-phase phosgene by observing the changes of fluorescence properties.

<Experimental Example 6> Evaluation 3 of Phosgene Detection Ability of the Compound of Example 2

The following experiment was performed to evaluate whether or not the compound of example 2 was useful for the detection of liquid-phase phosgene.

30 µg of the compound of example was absorbed in 30 mg of silica gel, which was treated with 3 µg or 30 µg of triphosgene dissolved in chloroform. Then, the changes of fluorescence properties were observed and one of the results is presented in FIG. 12.

FIG. 12 is a photograph illustrating the fluorescence characteristics of the silica gel retaining the compound of example 2 after the treatment of 30 µg triphosgene.

As shown in FIG. 12, fluorescence properties of the silica gel retaining the compound of example 2 treated with phosgene were changed, compared with the silica gel retaining the compound of example 2 not-treated with phosgene.

Therefore, it was confirmed that the compound of example 2 of the invention is effective in detecting liquid-phase phosgene by observing the changes of fluorescence properties.

In the above Experimental Examples 1-7, it was found that the compounds according to the present invention react with phosgene or DCP in a gaseous or liquid state to induce changes in fluorescence and color development at nM concentration, which induces different changes according to whether it is a phosgene or a DCP. Accordingly, the compounds of the invention or compositions containing the same may be usefully employed for phosgene and DCP detection, and can be used in the entire industry as a detection composition and a kit which are capable of selectively detecting and sensitively detecting to exposure of phosgene and DCP.

INDUSTRIAL APPLICABILITY

The compound for detecting phosgene and DCP (diethyl chlorophosphate) of the present invention can selectively detect phosgene and DCP (diethyl chlorophosphate) either in the liquid phase or gas phase by detecting the changes of fluorescence and color development very quickly within a few seconds with nM sensitivity. Therefore, the compound can be effectively used as a composition and a kit for the detection of one or more compounds selected from the group consisting of phosgene and DCP (diethyl chlorophosphate). In particular, it can be useful in the field where human resources must be protected from the exposure of phosgene and DCP (diethyl chlorophosphate).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

We claim:

1. A method for the detection of phosgene and/or diethyl chlorophosphate (DCP) comprising:
    contacting a compound represented by formula 1 below with a sample to be analyzed; and
    evaluating changes of fluorescence or absorption properties of the compound after contacting the compound with the sample:

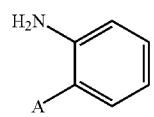

Formula 1 wherein A is

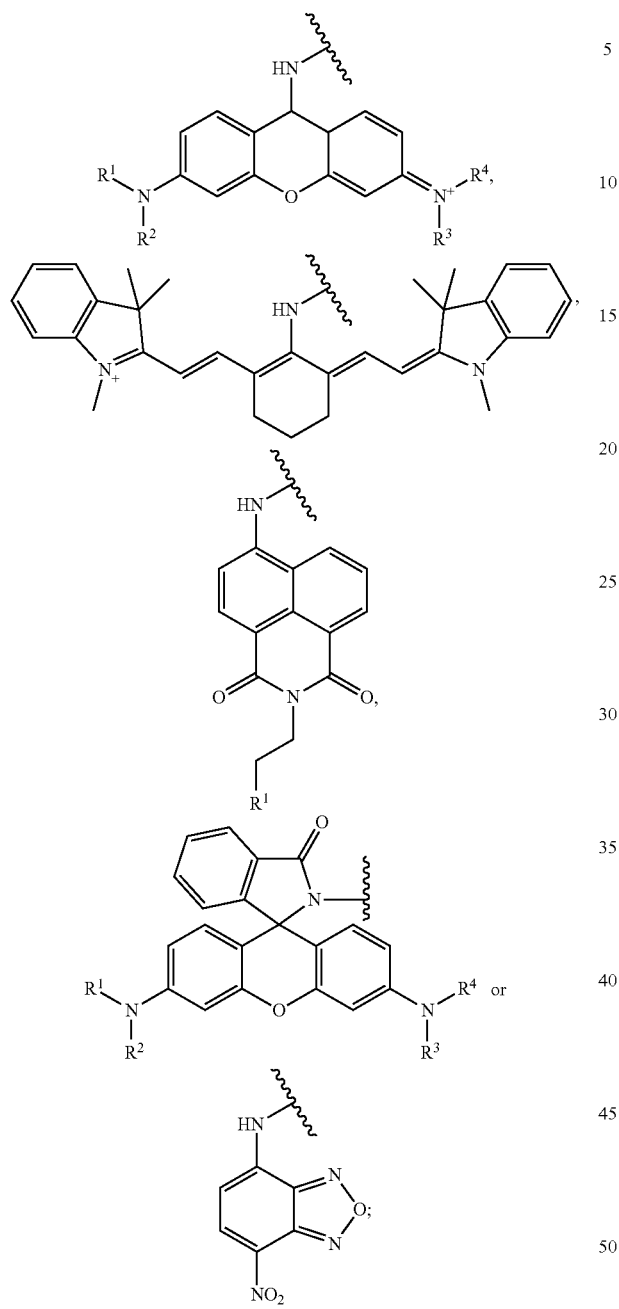

R[1] is —H, C1-10 straight or C3-10 branched alkyl, C1-10 straight or C3-10 branched alkoxy, or 4-7 membered heterocycloalkyl containing 1-3 hetero atoms selected from N, O, and S; and R[2], R[3] and R[4] are independently —H, C1-10 straight or C3-10 branched alkyl, or C1-10 straight or C3-10 branched alkoxy; and wherein the changes in fluorescence or absorption properties of the compound detect phosgene and/or DCP in the sample.

2. The method according to claim 1, wherein R[1] is —H, C1-5 straight or C3-5 branched alkyl, C1-5 straight or C3-5 branched alkoxy, or 4-6 membered heterocycloalkyl containing 2-3 hetero atoms selected from N, O, and S.

3. The method according to claim 1, wherein R[1] is C1-4 straight or C3-4 branched alkyl, or 6 membered heterocycloalkyl containing 2-3 hetero atoms selected from N, O, and S.

4. The method according to claim 1, wherein the compound represented by formula 1 above is the compound selected from the following compounds:

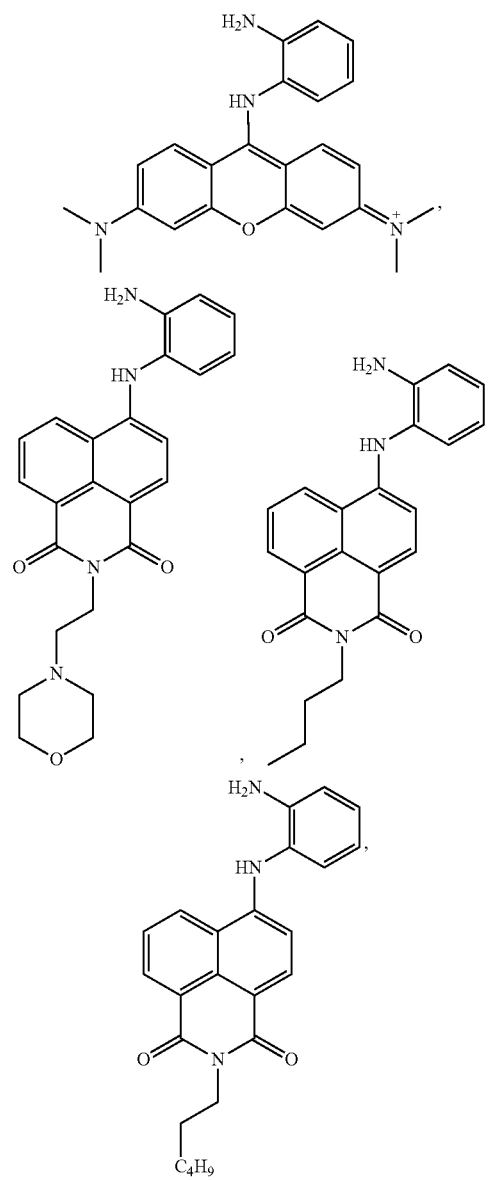

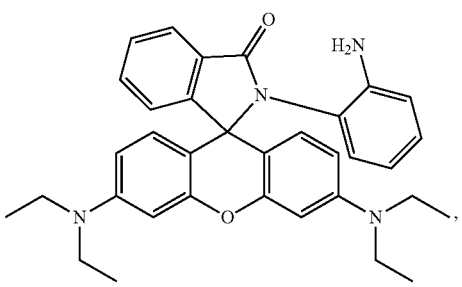

-continued

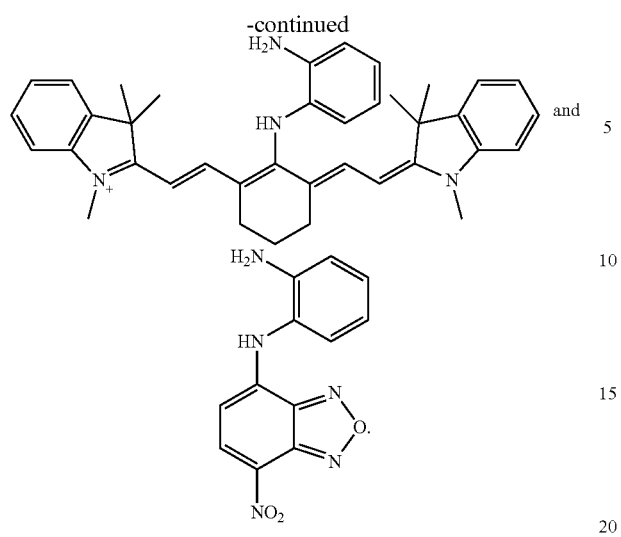

and

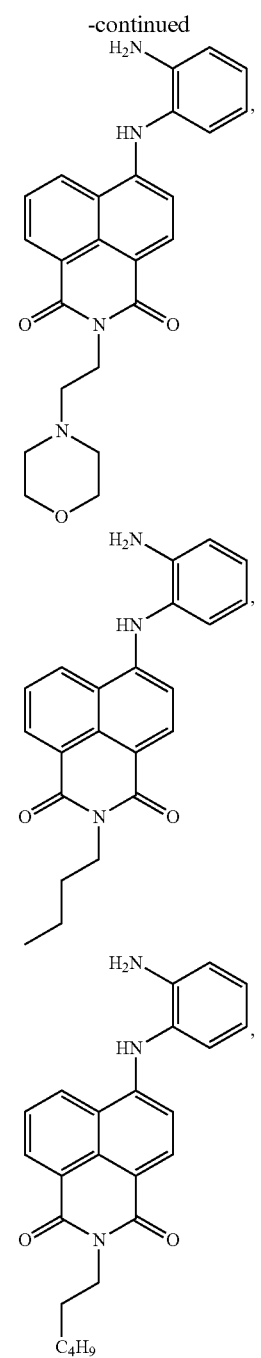

5. The method according to claim 1, wherein the compound is provided in a kit for the detection of phosgene and/or DCP.

6. The method according to claim 5, wherein the kit is capable of detecting changes of fluorescence or absorbance caused by the changes of Л-conjugation system of the compound, which results from nucleophilic attack of phenylenediamine included in the compound against phosgene or DCP.

7. The method of claim 1, wherein the method detects phosgene, and evaluating the fluorescence or absorption properties of the compound comprises detecting a yellow or purple fluorescence color in the presence of phosgene.

8. The method of claim 7, wherein the fluorescence color changes from yellow to a purple color as a concentration of phosgene increases.

9. The method of claim 1, wherein the method detects DCP, and evaluating the fluorescence or absorption properties of the compound comprises detecting a green fluorescence color in the presence of DCP.

10. The method of claim 9, wherein the green fluorescence color increases in intensity as a concentration of DCP increases.

11. The method of claim 1, wherein the method detects phosgene or DCP in a gas phase.

12. The method of claim 1, wherein the method detects phosgene or DCP in a liquid phase.

13. A method for the detection of phosgene and/or diethyl chlorophosphate (DCP), comprising:

contacting a gas or liquid sample to be analyzed with a compound selected from:

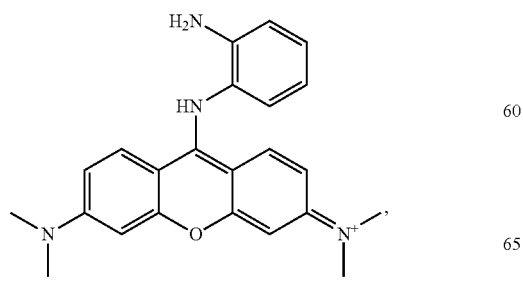

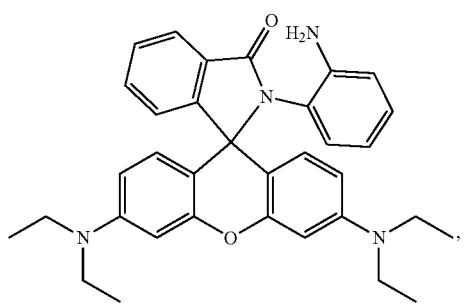

-continued
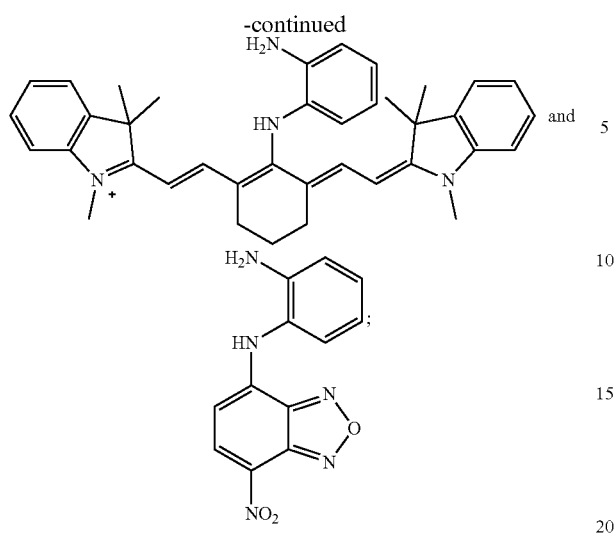
and
evaluating changes of fluorescence or absorption properties of the compound after contacting the compound with the sample, wherein a yellow or purple color fluorescence indicates presence of phosgene and a green color fluorescence indicates presence of DCP.
14. The method of claim 13, wherein the sample is a gas sample.
* * * * *